(12) United States Patent
Tegg

(10) Patent No.: US 9,375,550 B2
(45) Date of Patent: Jun. 28, 2016

(54) CATHETER ACTUATORS PROVIDING MECHANICAL ADVANTAGE

(71) Applicant: St. Jude Medical, Atrial Fibrillation Division, Inc., St. Paul, MN (US)

(72) Inventor: Troy T Tegg, Elk River, MN (US)

(73) Assignee: St. Jude Medical, Atrial Fibrillation Division, Inc., St. Paul, MN (US)

(*) Notice: Subject to any disclaimer, the term of this patent is extended or adjusted under 35 U.S.C. 154(b) by 499 days.

(21) Appl. No.: 13/840,176

(22) Filed: Mar. 15, 2013

(65) Prior Publication Data

US 2014/0276222 A1    Sep. 18, 2014

(51) Int. Cl.
*A61M 25/01* (2006.01)
*A61B 18/14* (2006.01)
*A61B 18/00* (2006.01)

(52) U.S. Cl.
CPC ........ *A61M 25/0136* (2013.01); *A61B 18/1492* (2013.01); *A61B 2018/00357* (2013.01); *A61B 2018/00577* (2013.01); *A61B 2018/00839* (2013.01); *A61M 25/0147* (2013.01)

(58) Field of Classification Search
CPC ..................... A61M 25/0147; A61M 25/0905; A61M 25/0136; A61B 18/1492; A61B 2018/00357; A61B 2018/00839; A61B 2018/00577
See application file for complete search history.

(56) References Cited

U.S. PATENT DOCUMENTS

| 5,195,968 | A | 3/1993 | Lundquist et al. |
| 5,254,088 | A | 10/1993 | Lundquist et al. |
| 5,273,535 | A | 12/1993 | Edwards et al. |
| 5,336,182 | A | 8/1994 | Lundquist et al. |
| 5,358,478 | A | 10/1994 | Thompson et al. |
| 5,383,852 | A | 1/1995 | Stevens-Wright |
| 5,395,327 | A | 3/1995 | Lundquist et al. |
| 5,462,527 | A | 10/1995 | Stevens-Wright et al. |
| 5,531,686 | A | 7/1996 | Lundquist et al. |
| 5,676,653 | A | 10/1997 | Taylor et al. |
| 5,702,433 | A | 12/1997 | Taylor et al. |
| 5,861,024 | A | 1/1999 | Rashidi |
| 5,891,088 | A | 4/1999 | Thompson et al. |
| 6,030,360 | A | 2/2000 | Biggs |
| 6,033,378 | A | 3/2000 | Lundquist et al. |
| 6,146,355 | A | 11/2000 | Biggs |
| 6,213,974 | B1 | 4/2001 | Smith et al. |
| 6,409,674 | B1 | 6/2002 | Brockway et al. |
| 6,485,455 | B1 | 11/2002 | Thompson et al. |
| 6,511,471 | B2 | 1/2003 | Rosenman et al. |
| 6,569,114 | B2 | 5/2003 | Ponzi et al. |
| 7,048,711 | B2 | 5/2006 | Rosenman et al. |
| 7,144,404 | B2 | 12/2006 | Whitson et al. |

(Continued)

*Primary Examiner* — Nathan R Price
*Assistant Examiner* — Melissa A Snyder
(74) *Attorney, Agent, or Firm* — Dykema Gossett PLLC

(57) ABSTRACT

Catheter actuators providing a mechanical advantage are disclosed. The actuators include a pull wire arm guide plate and a drive wheel attached around the pull wire arm guide plate and pivotable relative to the guide plate, the drive wheel comprising at least one thumb boss for pivoting the drive wheel about a drive wheel axis of rotation. The drive wheel mechanically engages at least one pull wire arm slidably mounted in a pull wire arm channel in the pull wire arm guide plate. A mechanism transfers drive wheel input into longitudinal motion of the at least one pull wire arm. The mechanism may include, for example, a pin pushing against a bendable pushing member riding in an arcuate pin groove in a top surface of the guide plate, or a pin pushing against a surface of a cam arm pivotably mounted on the top surface of the guide plate.

25 Claims, 17 Drawing Sheets

(56) References Cited

U.S. PATENT DOCUMENTS

| | | |
|---|---|---|
| 7,331,958 B2 | 2/2008 | Falwell et al. |
| 7,367,939 B2 | 5/2008 | Smith et al. |
| 7,374,553 B2 | 5/2008 | Koerner et al. |
| 7,377,906 B2 | 5/2008 | Selkee |
| 7,425,200 B2 | 9/2008 | Brockway et al. |
| 7,524,301 B2 | 4/2009 | Dubois et al. |
| 7,591,799 B2 | 9/2009 | Selkee |
| 7,606,609 B2 | 10/2009 | Muranushi et al. |
| 7,691,117 B2 | 4/2010 | Whitson et al. |
| 7,789,826 B2 | 9/2010 | Sullivan et al. |
| 7,862,503 B2 | 1/2011 | Smith et al. |
| 7,931,616 B2 | 4/2011 | Selkee |
| 8,021,327 B2 | 9/2011 | Selkee |
| 8,043,288 B2 | 10/2011 | Dando et al. |
| 8,066,664 B2 | 11/2011 | LaDuca et al. |
| 8,137,308 B2 | 3/2012 | Schultz |
| 8,216,255 B2 | 7/2012 | Smith et al. |
| 8,252,019 B2 | 8/2012 | Fleming, III |
| 8,287,448 B2 | 10/2012 | Schaaf |
| 8,348,888 B2 | 1/2013 | Selkee |
| 8,366,607 B2 | 2/2013 | Sullivan et al. |
| 8,376,990 B2 | 2/2013 | Ponzi et al. |
| 8,377,050 B2 | 2/2013 | Lentz et al. |
| 2004/0106897 A1 | 6/2004 | Thompson et al. |
| 2005/0096590 A1* | 5/2005 | Gullickson et al. ........ 604/95.04 |
| 2005/0159789 A1 | 7/2005 | Brockway et al. |
| 2005/0288551 A1 | 12/2005 | Calister et al. |
| 2006/0142695 A1 | 6/2006 | Knudson |
| 2006/0149295 A1 | 7/2006 | Fleming, III |
| 2006/0252993 A1 | 11/2006 | Freed et al. |
| 2007/0055172 A1 | 3/2007 | Ratnakar |
| 2008/0188868 A1 | 8/2008 | Weitzner et al. |
| 2008/0188869 A1 | 8/2008 | Weitzner et al. |
| 2008/0188890 A1 | 8/2008 | Weitzner et al. |
| 2008/0221391 A1 | 9/2008 | Weitzner et al. |
| 2008/0243115 A1 | 10/2008 | Ogle |
| 2008/0287862 A1 | 11/2008 | Weitzne et al. |
| 2008/0300574 A1 | 12/2008 | Belson et al. |
| 2009/0281379 A1 | 11/2009 | Binmoeller et al. |
| 2010/0094310 A1 | 4/2010 | Warring et al. |
| 2010/0168827 A1 | 7/2010 | Schultz |
| 2011/0028894 A1 | 2/2011 | Foley et al. |
| 2011/0077498 A1 | 3/2011 | McDaniel |
| 2011/0105954 A1 | 5/2011 | Cohen et al. |
| 2011/0213300 A1 | 9/2011 | McWeeney et al. |
| 2011/0218536 A1 | 9/2011 | Wunderlich |
| 2011/0230947 A1 | 9/2011 | Hartley et al. |
| 2011/0270172 A1 | 11/2011 | Selkee |
| 2011/0301592 A1 | 12/2011 | Kerr et al. |
| 2011/0301603 A1 | 12/2011 | Kerr et al. |
| 2011/0301604 A1 | 12/2011 | Horner et al. |
| 2012/0004502 A1 | 1/2012 | Weitzner et al. |
| 2012/0078080 A1 | 3/2012 | Foley et al. |
| 2012/0123327 A1 | 5/2012 | Miller |
| 2012/0143088 A1 | 6/2012 | Schultz |
| 2012/0158043 A1 | 6/2012 | Suzuki |
| 2012/0184955 A1 | 7/2012 | Pivotto et al. |
| 2012/0209143 A1 | 8/2012 | Schultz |
| 2013/0046236 A1 | 2/2013 | Ponzi et al. |

* cited by examiner

CATHETER ACTUATORS PROVIDING MECHANICAL ADVANTAGE

BACKGROUND OF THE INVENTION a. Field of the Invention

The instant invention relates to actuators for steerable medical devices. In particular, the instant invention relates to actuators providing a mechanical advantage in steerable medical devices employing one or more pull wires.

b. Background Art

Electrophysiology catheters are used in a variety of diagnostic, therapeutic, and/or mapping and ablative procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions, and stasis of blood flow in a chamber of a heart, which can lead to a variety of symptomatic and asymptomatic ailments and even death.

Typically, a catheter is deployed and manipulated through a patient's vasculature to the intended site, for example, a site within a patient's heart. The catheter typically carries one or more electrodes that can be used for cardiac mapping or diagnosis, ablation, and/or other therapy delivery modes, or both, for example. Once at the intended site, treatment can include, for example, radio frequency (RF) ablation, cryoablation, laser ablation, chemical ablation, high-intensity focused ultrasound-based ablation, microwave ablation, and/or other ablation treatments. The catheter imparts ablative energy to cardiac tissue to create one or more lesions in the cardiac tissue. These lesions disrupt undesirable cardiac activation pathways and thereby limit, corral, or prevent errant conduction signals that can form the basis for arrhythmias.

To position a catheter within the body at a desired site, some type of navigation must be used, such as using mechanical steering features incorporated into the catheter (or an introducer sheath). In some examples, medical personnel may manually manipulate and/or operate the catheter using the mechanical steering features.

In order to facilitate the advancement of catheters through a patient's vasculature, the simultaneous application of torque at the proximal end of the catheter and the ability to selectively deflect the distal tip of the catheter in a desired direction can permit medical personnel to adjust the direction of advancement of the distal end of the catheter and to selectively position the distal portion of the catheter during an electrophysiological procedure. The proximal end of the catheter can be manipulated to guide the catheter through a patient's vasculature. The distal tip can be deflected by a pull wire attached at the distal end of the catheter and extending proximally to an actuator in a control handle that controls the application of tension on the pull wire.

The foregoing discussion is intended only to illustrate the present field and should not be taken as a disavowal of claim scope.

BRIEF SUMMARY OF THE INVENTION

It is desirable to be able to compensate or adjust for the increased force that a clinician may be required to apply to an actuator of a deflectable medical device as the amount of deflection at a distal end of the medical device increases. It is also desirable to be able to tailor the input force required to deflect a distal portion of a medical device employing pull wires.

In one embodiment, a pull wire actuator comprises (a) a pull wire arm guide plate adapted to be mounted in a handle housing, wherein the pull wire arm guide plate comprises a top surface and a bottom surface; a first arm channel in the top surface, wherein the first arm channel has a distal end and a proximal end; and a first arcuate pin groove in the top surface, wherein the first arcuate pin groove extends from a first end to a second end, wherein the second end meets the distal end of the first arm channel. The pull wire actuator, in this embodiment, further comprises a drive wheel attached around the pull wire arm guide plate and pivotable relative to the pull wire arm guide plate, wherein the drive wheel comprises first and second thumb bosses for pivoting the drive wheel about a drive wheel axis of rotation. This pull wire actuator further comprises a first pull wire arm slidably mounted in the first arm channel and comprising a proximal end and a distal end; and a first sliding pin carrier slidably disposed on the top surface of the pull wire arm guide plate, the first sliding pin carrier comprising a first pushing pin riding in the first arcuate pin groove. Finally, in this embodiment, a first bendable pushing member is slidably positioned in the first arcuate pin groove between the first pushing pin and the distal end of the first pull wire arm.

In various embodiments, the pull wire actuator includes a first arcuate pin groove that is radially offset from a drive wheel axis of rotation by a radial distance, and the radial distance decreases moving from the first end toward the second end of the first arcuate pin groove.

In another embodiment, a control handle comprises the following: (a) a handle upper housing and a handle lower housing together defining a handle housing; (b) a pull wire arm guide plate mounted in the handle housing, wherein the pull wire arm guide plate comprises the following: (i) a top surface and a bottom surface; (ii) a first arm channel in the top surface, wherein the first arm channel has a distal end and a proximal end; and (iii) a first arcuate pin groove in the top surface, wherein the first arcuate pin groove extends from a first end to a second end, and wherein the second end meets the distal end of the first arm channel; (c) a drive wheel attached around the pull wire arm guide plate and pivotable in the handle housing relative to the pull wire arm guide plate, wherein the drive wheel comprises first and second thumb bosses for pivoting the drive about a drive wheel axis of rotation; (d) a first pull wire arm slidably mounted in the first arm channel and comprising a proximal end and a distal end; (e) a sliding pin carrier slidably disposed on the top surface of the pull wire arm guide plate, the sliding pin carrier comprising a first pushing pin riding in the first arcuate pin groove; and (f) a first bendable pushing member slidably positioned in the first arcuate pin groove between the first pushing pin and the distal end of said first pull wire arm.

In at least one embodiment, a pull wire actuator comprises the following: (a) a pull wire arm guide plate adapted to be mounted in a handle housing, wherein the pull wire arm guide plate comprises the following: (i) a top surface and a bottom surface; (ii) a first arm channel in the top surface, wherein the first arm channel has a distal end and a proximal end; and (iii) a first longitudinally-extending pin channel through the top surface, wherein the pin channel extends from a distal end to a proximal end; (b) a drive wheel attached around the pull wire arm guide plate and pivotable relative to the pull wire arm guide plate, wherein the drive wheel comprises (i) first and second thumb bosses for pivoting the drive wheel about a drive wheel axis of rotation, and (ii) a first pushing pin; (c) a first pull wire arm slidably mounted in the first arm channel, wherein the first pull wire arm comprises a proximal end, a distal end, and a first pushed pin riding in the first longitudinally-extending pin channel; and (d) a first cam arm pivotally mounted on the top surface of the pull wire arm guide plate at a first pivot pin, wherein the first pivot pin is both laterally and longitudinally offset from the drive wheel axis of rotation, and wherein the first cam arm comprises (i) a first pushing surface adapted to push against the first pushed pin, and (ii) a first pushed surface against which the first pushing pin is adapted to push.

In various embodiments, the first pivot pin is positioned so that the mechanical advantage increases as the drive wheel is rotated from a catheter-neutral orientation to a catheter-deflected orientation. For example, the first pivot pin may be positioned laterally and proximally of said drive wheel axis of rotation.

In another embodiment, a control handle comprising the following: (a) a handle upper housing and a handle lower housing together defining a handle housing; (b) a pull wire arm guide plate mounted in the handle housing, wherein the pull wire arm guide plate comprises the following: (i) a top surface and a bottom surface; (ii) a first arm channel in the top surface, wherein the first arm channel has a distal end and a proximal end; and (iii) a first longitudinally-extending pin channel through the top surface, wherein the pin channel extends from a distal end to a proximal end; (c) a drive wheel attached around the pull wire arm guide plate and pivotable relative to the pull wire arm guide plate, wherein the drive wheel comprises (i) first and second thumb bosses for pivoting the drive wheel about a drive wheel axis of rotation, and (ii) a first pushing pin; (d) a first pull wire arm slidably mounted in the first arm channel, wherein the first pull wire arm comprises a proximal end, a distal end, and a first pushed pin riding in the first longitudinally-extending pin channel; and (e) a first cam arm pivotally mounted on the top surface of the pull wire arm guide plate at a first pivot pin, wherein the first pivot pin is both laterally and longitudinally offset from the drive wheel axis of rotation, and wherein the first cam arm comprises (i) a first pushing surface adapted to push against the first pushed pin, and (ii) a first pushed surface against which the first pushing pin is adapted to push.

In yet another embodiment, a medical device handle is provided that includes a manipulatable actuator, having an axis of rotation, and a bendable pushing member movable with rotation of the manipulatable actuator. A channel is contoured to arcuately advance a back portion of the bendable pushing member along a generally decreasing radial path relative to the axis of rotation of the manipulatable actuator, and contoured to direct a remaining portion of the bendable pushing member from its generally decreasing radial path to a substantially linear path oriented longitudinally through the medical device handle. A pull wire is coupled to the remaining portion of the bendable pushing member that is oriented longitudinally through the medical device handle, and directed substantially longitudinally through a distal end of the medical device handle.

The foregoing and other aspects, features, details, utilities, and advantages of the present invention will be apparent from reading the following description and claims, and from reviewing the accompanying drawings.

DETAILED DESCRIPTION OF THE INVENTION

Figure 1:
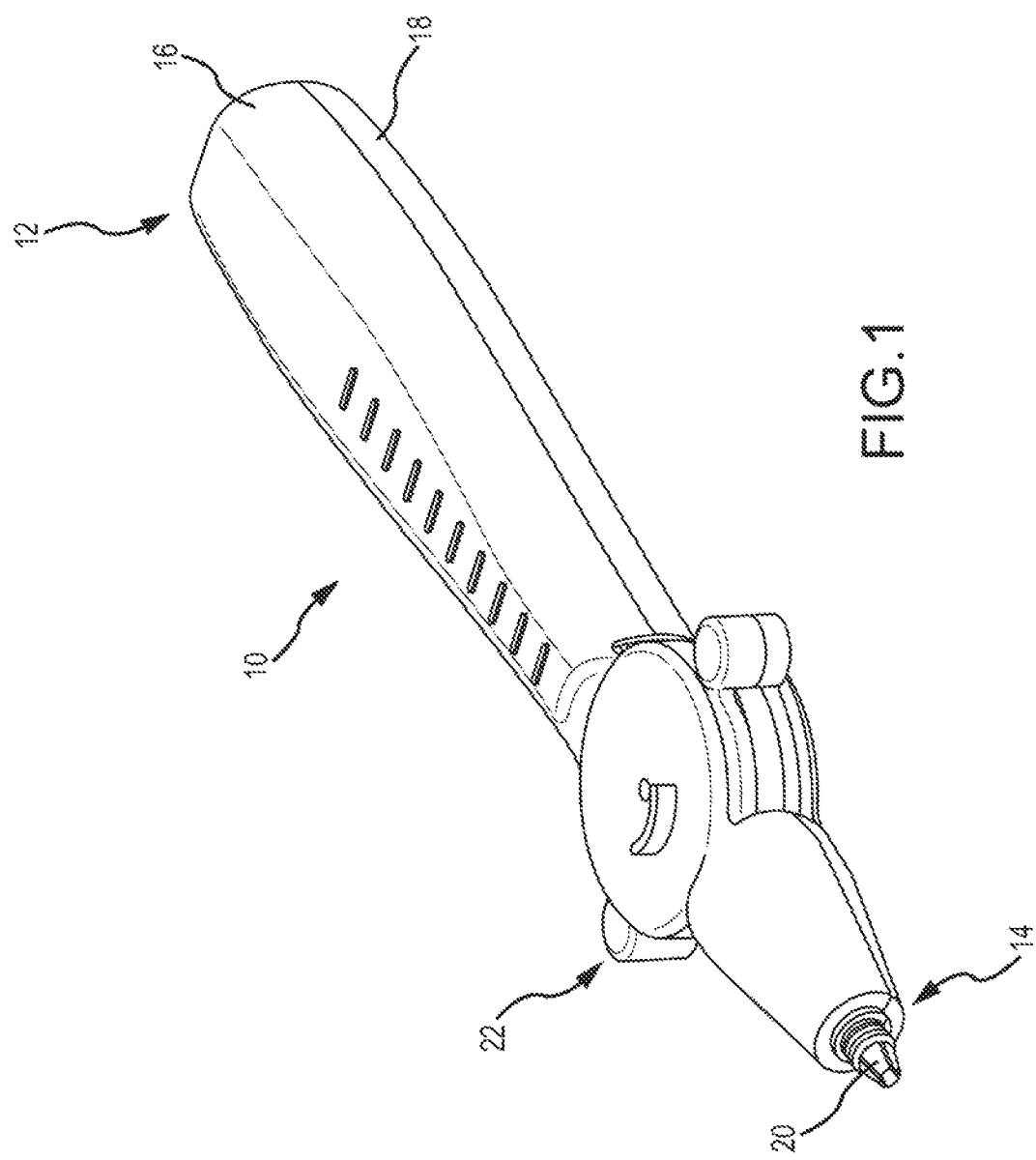
FIG. 1 is an isometric view of a control handle for a steerable diagnostic or ablation catheter.

Referring now to the figures, in which like reference numerals refer to the same or similar features in the various views, FIG. 1 depicts a control handle 10 for a catheter according to a first embodiment. The catheter may be, for example, a diagnostic catheter or an ablation catheter. The control handle 10 includes a proximal end 12 and a distal end 14. It also includes a handle upper housing 16 and a handle lower housing 18. Also visible in FIG. 1, at the distal end 14, is a strain relief 20. The deflectable catheter shaft (not shown) would extend distally from the distal end of the handle toward a working end (e.g., an ablation tip or a diagnostic tip) of the catheter. Clearly visible in FIG. 1 is a pull wire actuator 22 mounted between the handle upper housing 16 and the handle lower housing 18.

Figure 2:
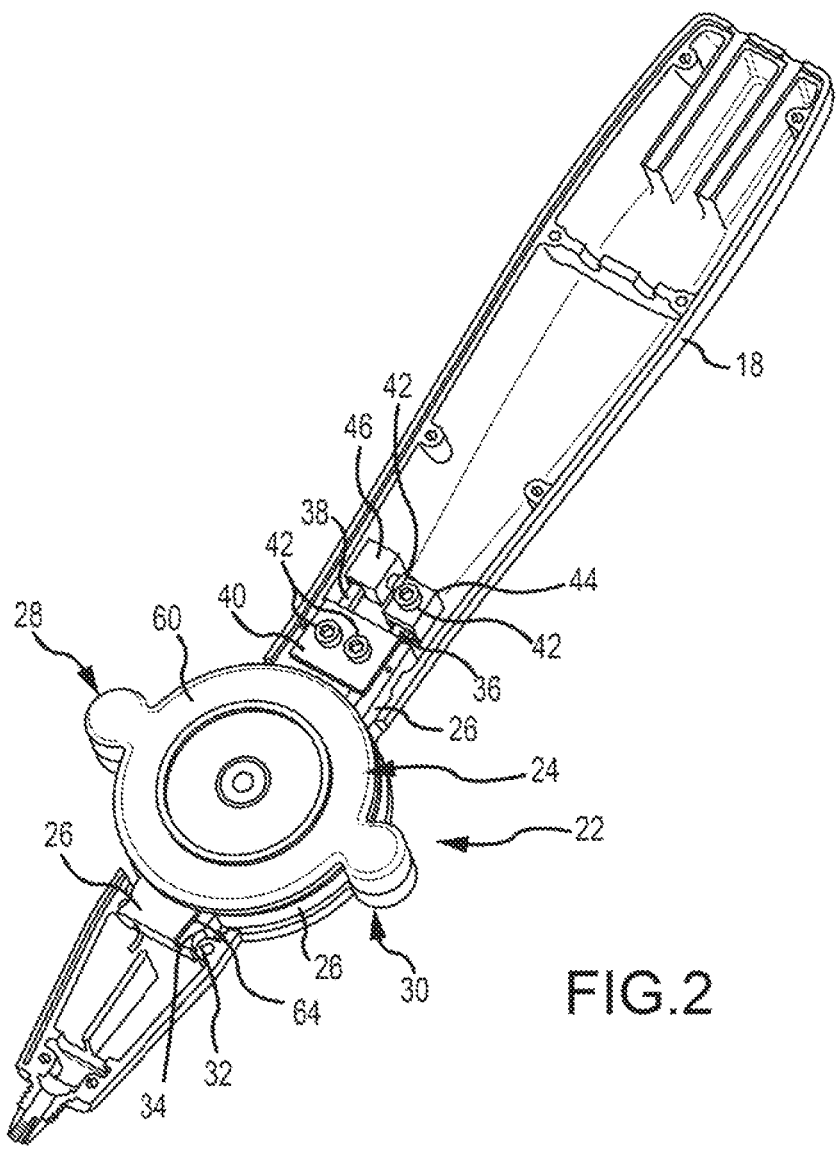
FIG. 2 is an isometric view of the control handle depicted in FIG. 1, but with the handle upper housing removed, revealing a pull wire actuator mounted to a handle lower housing.

In FIG. 2, the handle upper housing 16 shown in FIG. 1 has been removed to reveal details about the inner workings of this representative catheter handle. The pull wire actuator 22 comprises a drive wheel 24 that clamps around or sandwiches a pull wire arm guide plate 26. The drive wheel 24, which may be rotated relative to the upper and lower handle housings 16, 18, includes a first thumb boss 28 and a second thumb boss 30. The pull wire arm guide plate 26 is fixedly retained in the handle housing as shown. For instance, the lower handle housing 18 includes protuberances 32 engaged in corresponding recesses 34 in the pull wire arm guide plate 26. A first pull wire arm 36 and a second pull wire arm 38 may also be seen in FIG. 2. An upper pull wire arm retention plate 40 is shown affixed to the pull wire arm guide plate 26 by a pair of cap screws 42. This retention plate 40 could, in an alternative embodiment (not shown), be molded into the pull wire guide plate 26, eliminating the need for the two cap screws 42 shown attaching the retention plate in FIG. 2. A first pull wire clamp 44 is depicted affixed to the first pull wire arm 36 by a cap screw 42. Similarly, a second pull wire clamp 46 is depicted affixed to the proximal end of the second pull wire arm 38 by another cap screw 42.

Figure 3:
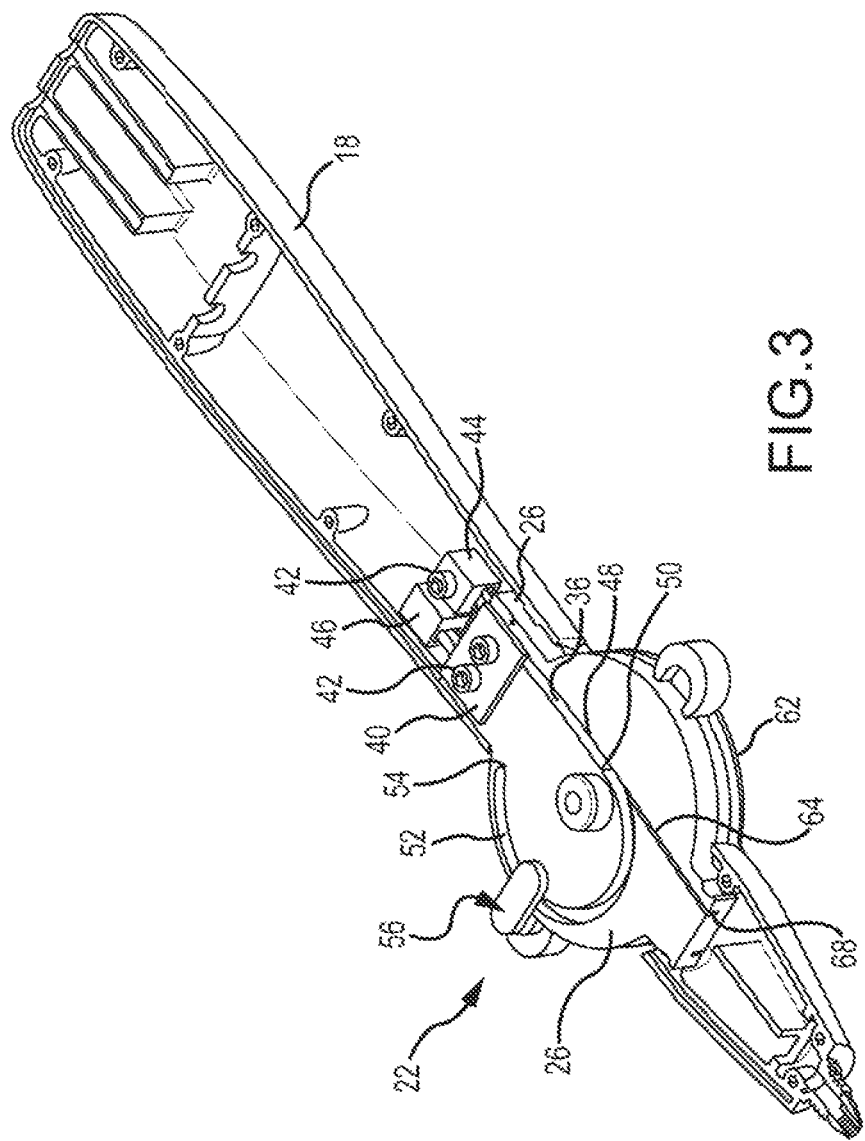
FIG. 3 depicts the control handle of FIGS. 1 and 2, with the upper handle housing removed and the top half of the drive wheel removed, revealing a pull wire arm guide plate mounted in the handle lower housing.

FIG. 3 is similar to FIGS. 1 and 2; however, in FIG. 3, the top half of the drive wheel has also been removed to show details in the top surface of the pull wire arm guide plate 26. As shown in this figure, the first pull wire arm 36 slides in an arm channel 48. In this figure, the distal end 50 of the first pull wire arm 36 is shown at the distal end of the arm channel 48. An arcuate pin groove 52 is also visible in FIG. 3. This pin groove 52 extends from a dead end 54 to the distal end of the arm channel 48. A sliding pin carrier (or "slider") 56 is shown riding on the top surface of the pull wire arm guide plate 26 with its downwardly-extending pin 58 (not visible in FIG. 3, but shown in, for example, FIGS. 6 and 7) riding in the pin groove 52.

Figure 4:
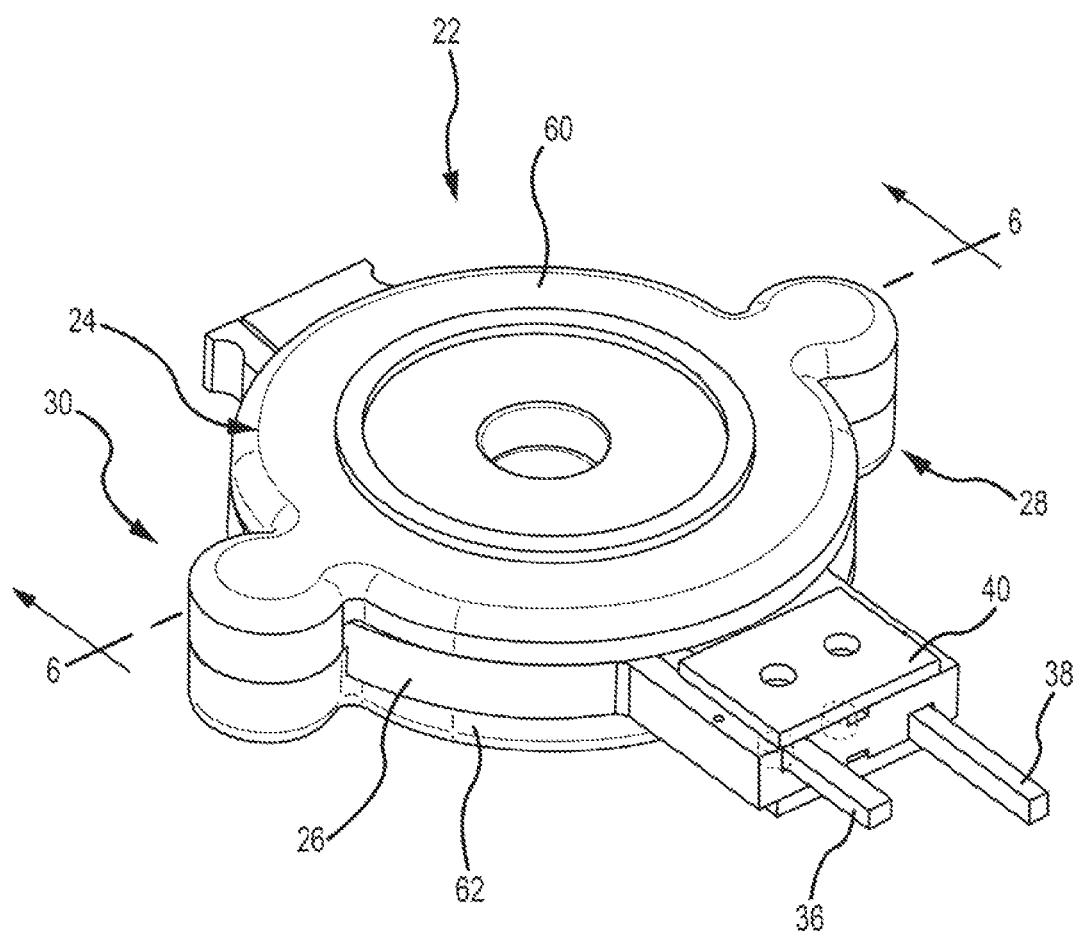
FIG. 4 is an isometric view depicting the pull wire actuator shown in FIGS. 1-3 isolated from the control handle housing.

FIG. 4 is an isometric view of the pull wire actuator 22 depicted in FIGS. 1-3, but isolated from the entire handle housing. This isometric view clearly shows a two-part drive wheel 24, which includes a top half 60 and a bottom half 62. The top half 60 of the drive wheel 24 mates with the bottom half 62 of the drive wheel 24 to create a first thumb boss 28 and a second thumb boss 30. When assembled as shown in FIG. 4, the top half 60 of the drive wheel 24 and the bottom half 62 of the drive wheel 24 clamp around the pull wire arm guide plate 26. In this manner, when the pull wire arm guide plate 26 is held from motion by the handle lower and upper housings 18, 16, respectively, the drive wheel may be pivoted clockwise and counterclockwise relative to the pull wire arm guide plate 26. As will be explained further below, this pivoting motion of the drive wheel 24 results in corresponding longitudinal motion of the first pull wire arm 36 and the second pull wire arm 38 which, in turn, creates tension in and releases tension from the pull wires that are affixed to the first and second pull wire arms. In this pull wire actuator 22, one pull wire is attached to the first pull wire arm 36 and a second pull wire is attached to the second pull wire arm 38. When the first pull wire arm is moved proximally in the handle housing, which is downwardly and rightwardly as depicted in FIG. 4, that would displace the first pull wire rearwardly, thus resulting in deflection of the catheter shaft in a first direction. When the drive wheel is rotated clockwise as depicted in FIG. 4, the second pull wire arm would be displaced proximally, which is downwardly and to the right as depicted in FIG. 4, which would, in turn, pull the second pull wire, thereby deflecting the catheter shaft in a second direction.

Figure 5:
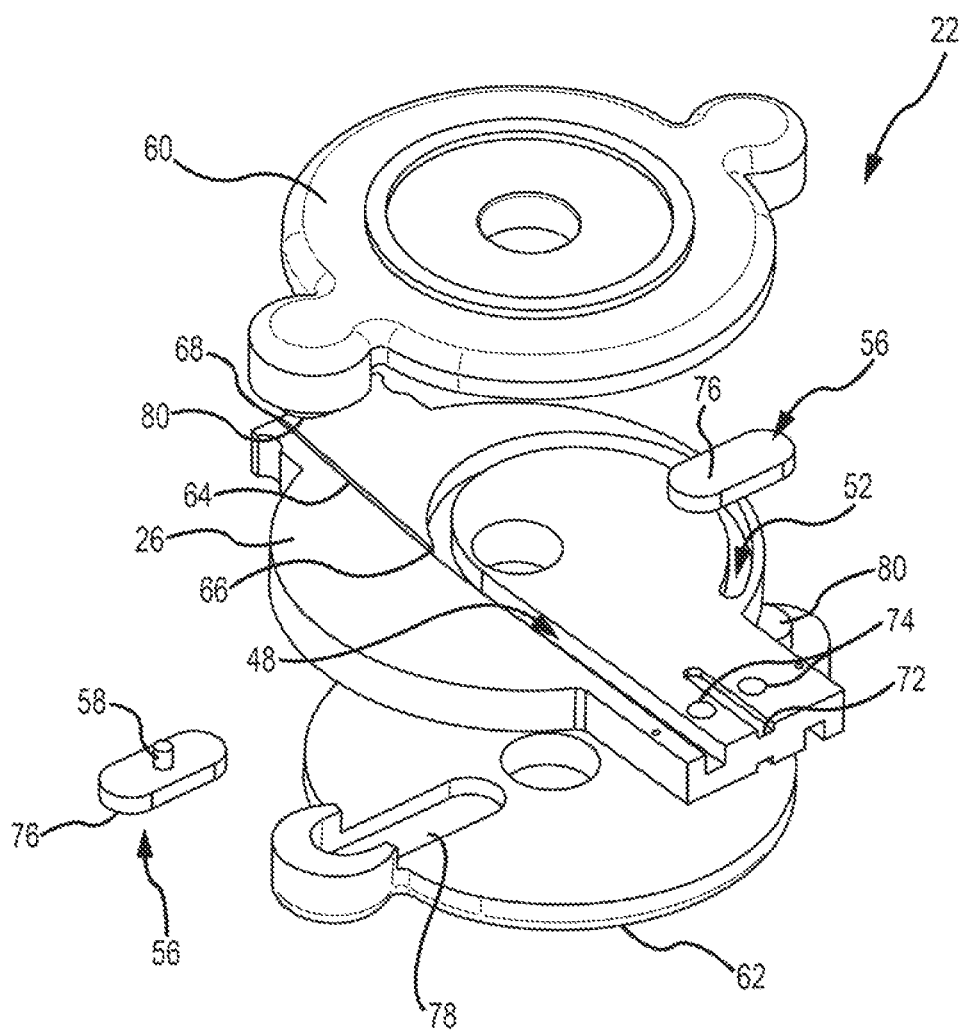
FIG. 5 is an exploded view of the pull wire actuator depicted in, for example, FIGS. 2 and 4, with some components removed for clarity.

FIG. 5 is an exploded, isometric view of the pull wire actuator 22 depicted in, for example, FIG. 4. In this figure, the top half 60 of the drive wheel is exploded away from the top surface of the pull wire arm guide plate 26, and the bottom half 62 of the drive wheel is exploded downwardly away from the bottom surface of the pull wire arm guide plate. In one embodiment, the top surface of the pull wire arm guide plate 26, including all of the channels, grooves, and slots formed therein, is a mirror image of the bottom surface (not shown) of the pull wire arm guide plate, to accommodate a second pull wire arm and an additional pull wire to facilitate bidirectional steering.

In another embodiment, a plurality of pull wire arm guide plates 26 could be stacked rather than, or in addition to, using a mirrored image on the top and bottom surfaces of a single pull wire arm guide plate 26. For example, a first pull wire arm guide plate 26 could accommodate a first pull wire for deflection in a first direction, and a second pull wire arm guide 26 could accommodate a second pull wire for deflection in a second direction, much like a single pull wire arm guide 26 with mirrored top and bottom surfaces could accommodate first and second pull wires for deflection in first and second directions. More generally, it should be noted that more than one pull wire arm guide plate 26, each with one or more sides configured to actuate a respective pull wire, may be used to accommodate deflection in a number of directions corresponding to the number of pull wires. For example, two stacked pull wire arm guide plates 26, each having mirrored top and bottom images, could accommodate four pull wires and at least four directions of deflection with the use of at least one additional set of thumb bosses or other actuation mechanism.

In FIG. 5, the first and second pull wire arms have been removed from their respective arm channels (e.g., 48). An upper pull wire slot 64 is clearly visible in the upper left portion of the pull wire arm guide plate 26 depicted in FIG. 5. This pull wire slot intersects the pin groove 52 approximately where the pin groove, in turn, intersects the arm channel 48. The pull wire slot 64 includes a proximal end 66 and a distal end 68. A pull wire extends distally from the distal end 68 of the pull wire slot 64 toward the working end of the catheter (i.e., the distal end of the catheter that performs the diagnostic or therapeutic function). The pull wire would also extend proximally from the proximal end 66 of the pull wire slot 64, through the arm channel 48 to the proximal end of the pull wire arm where the pull wire is clamped to the pull wire arm 36 as explained further below. The upper pull wire arm retention plate 40 (see FIG. 4) may include a longitudinally-extending rib 70 on its lower surface (see, for example, FIG. 10). That longitudinally-extending rib 70 helps to align and stabilize the retention plate 40, and that rib would ride in a slot 72 depicted in FIG. 5. The cap screws 42 for retaining the upper pull wire arm retention plate 40 would thread into the holes 74 depicted in the top surface of the pull wire arm guide plate 26 in FIG. 5. In FIG. 5, the lower sliding pin carrier (or "slider") 56 is shown exploded away from the remaining components. This slider 56 includes an elongated plate 76 and a push pin 58. The elongated plate 76 slides in a plate channel 78 in the bottom half of the drive wheel 62. A plate positioner (just visible in FIG. 5) helps to position and retain the elongated plate 76 of the sliding pin carrier 56 in the plate channel 78. The top slider 56 is also visible in FIG. 5, having its push pin 58 (not visible in FIG. 5) riding in the pin groove 52. The top half of the drive wheel 60 is a mirror image of the bottom half 62 of the drive wheel. Thus, the top slider 56 slides in a plate channel 78 in the top half 60 of the drive wheel, much like the lower slider 56 slides in the plate channel 78 in the bottom half 62 of the drive wheel.

Figure 6:
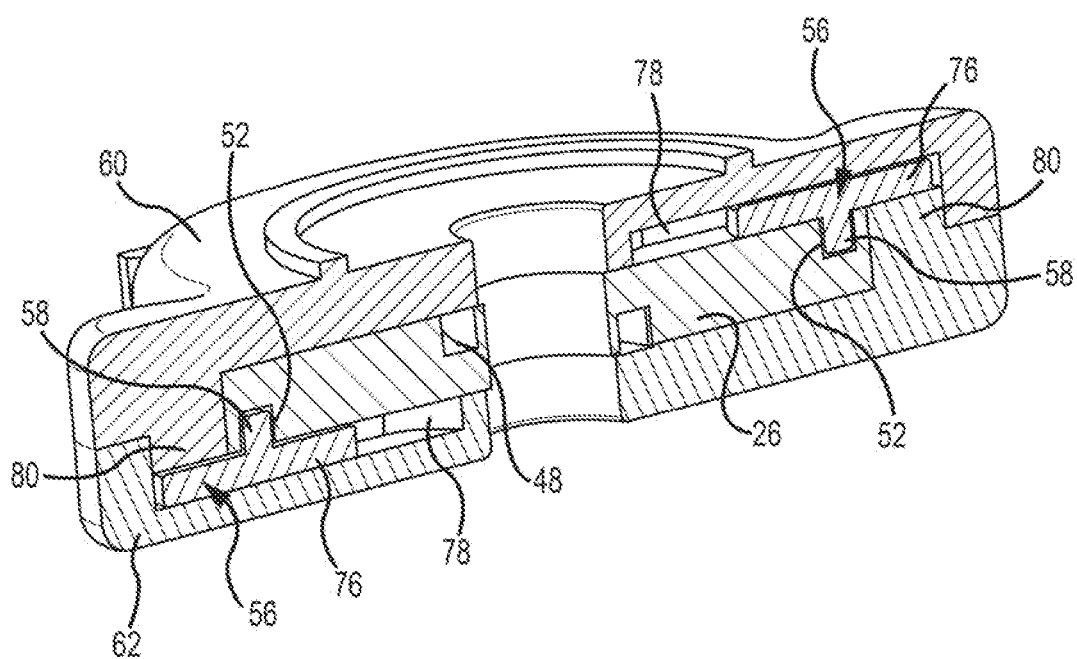
FIG. 6 is an isometric, cross-sectional view taken along line 6-6 of FIG. 4.

FIG. 6 is an isometric, cross-sectional view taken along line 6-6 of FIG. 4. This figure clearly shows how the top half 60 of the drive wheel 24 and the bottom half 62 of the drive wheel 24 sandwich between them the pull wire arm guide plate 26. This figure also clearly shows how, in the assembled pull wire actuator 22, the push pins 58 extending from their respective elongated plates 76 ride in their respective pin grooves 52, one of which is in the top surface of the pull wire arm guide plate 26 and the other of which is formed in the lower surface of the pull wire arm guide plate 26. As will be discussed further below, an elongated plate 76 of a sliding pin carrier 56 is adapted to slide radially in a plate channel 78 as the drive wheel is rotated around the pull wire arm guide plate 26. It may also be clearly seen in FIG. 6 how plate positioner 80 extending downwardly from the top half 60 of the drive wheel 24 helps maintain the elongated plate 76 of the lower sliding pin carrier 56 in the plate channel 78 formed in the bottom half 62 of the drive wheel 24. A similar plate positioner 80 is formed as part of the bottom half 62 of the drive wheel 24 and helps maintain the elongated plate 76 of the upper sliding pin carrier 56 in the corresponding plate channel 78 formed in the top half 60 of the drive wheel 24. In the handle orientation depicted in FIG. 6, each of the sliding pin carriers 56 is resting in nearly the most outwardly-possible position in its respective plate channel 78. As the drive wheel 24 is rotated in different directions about the pull wire arm guide plate 26, the sliding pin carriers 56 slide radially inwardly and outwardly in their respective plate channels 78.

Figure 7:
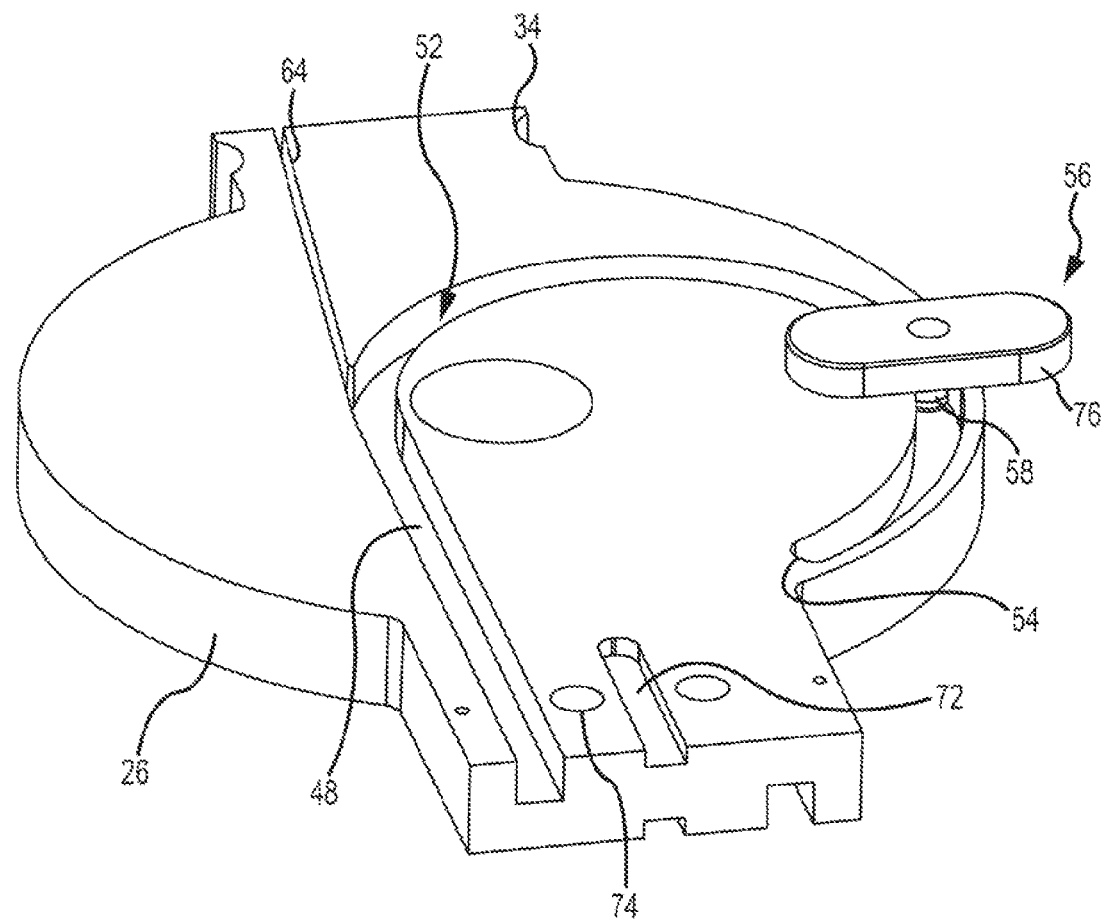
FIG. 7 is an isometric view showing the top surface of the pull wire arm guide plate, showing a sliding pin carrier riding in a groove.
Figure 8:
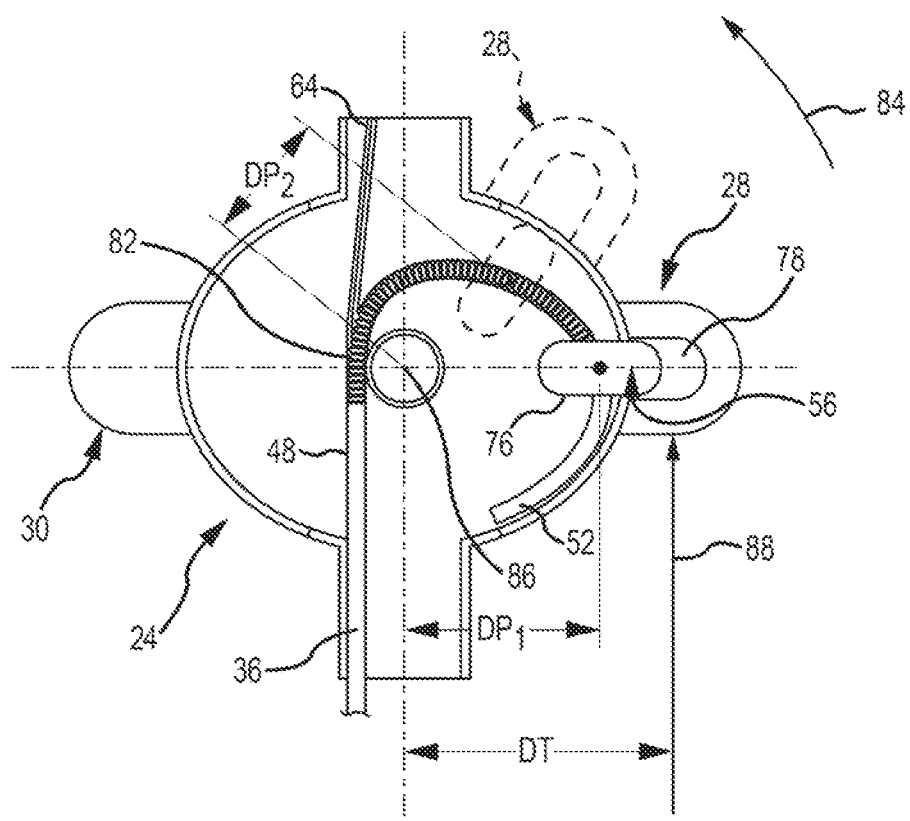
FIG. 8 is a plan view depicting the pull wire arm guide plate with a sliding pin carrier, a bendable pushing member, and a pull wire arm in place.

FIG. 7 is another isometric view of the pull wire arm guide plate 26. In this figure, the upper sliding pin carrier 56 is shown with its respective push pin 58 (the location of the top end of the pin 58 is represented in FIG. 8 as a dark circle centrally located on the elongated plate 76) riding in the pin groove 52 formed in the top surface of the pull wire arm guide plate 26. This figure again shows how the pull wire slot 64 intersects the pin groove 52 adjacent to the location where the pin groove intersects the distal end of the arm channel 48.

As clearly shown in FIG. 8, during operation of the pull wire actuator 22 according to this embodiment, a bendable pushing member 82 (e.g., a coil spring or a Nitonol rod) is positioned in the pin groove 52 between the push pin 58 extending downwardly from the top sliding pin carrier 56 and the distal end of the pull wire arm 36. As the thumb boss 28 on the right side of FIG. 8 is rotated in the direction of the arrow 84 (i.e., counterclockwise in this figure), the push pin is guided by the pin groove 52 and pushes on an end of the bendable pushing member 82. This drives the bendable pushing member counterclockwise in FIG. 8 in the pin groove, causing it to exert a force on the distal end of the pull wire arm 36, thereby driving the pull wire arm proximally in the catheter handle 10.

As may be clearly seen in FIG. 8, the distance between the push pin 58 and the axis of rotation 86 decreases as the right hand thumb boss 28 is rotated in the direction of the arrow 84. In particular, the pin groove 52 is configured to move the pin 58 closer to the axis of rotation as the bendable pushing member 82 drives the pull wire arm 36 proximally. Simultaneously, the elongated plate 76 comprising part of the sliding pin carrier 56 moves radially inwardly in its plate channel 78. As may be clearly seen in this figure, a distance DT from the axis of rotation 86 to the thumb boss 28 where the clinician applies thumb force 88 does not change, whereas the distance DP from the axis of rotation 86 to the pin 58 becomes shorter (e.g., compare $DP_1$ to $DP_2$) as the drive wheel is rotated in the direction of the arrow 84 in FIG. 8. Thus, the mechanical advantage increases as the thumb boss 28 is rotated from the three o'clock position to the one o'clock position in FIG. 8.

Figure 9:
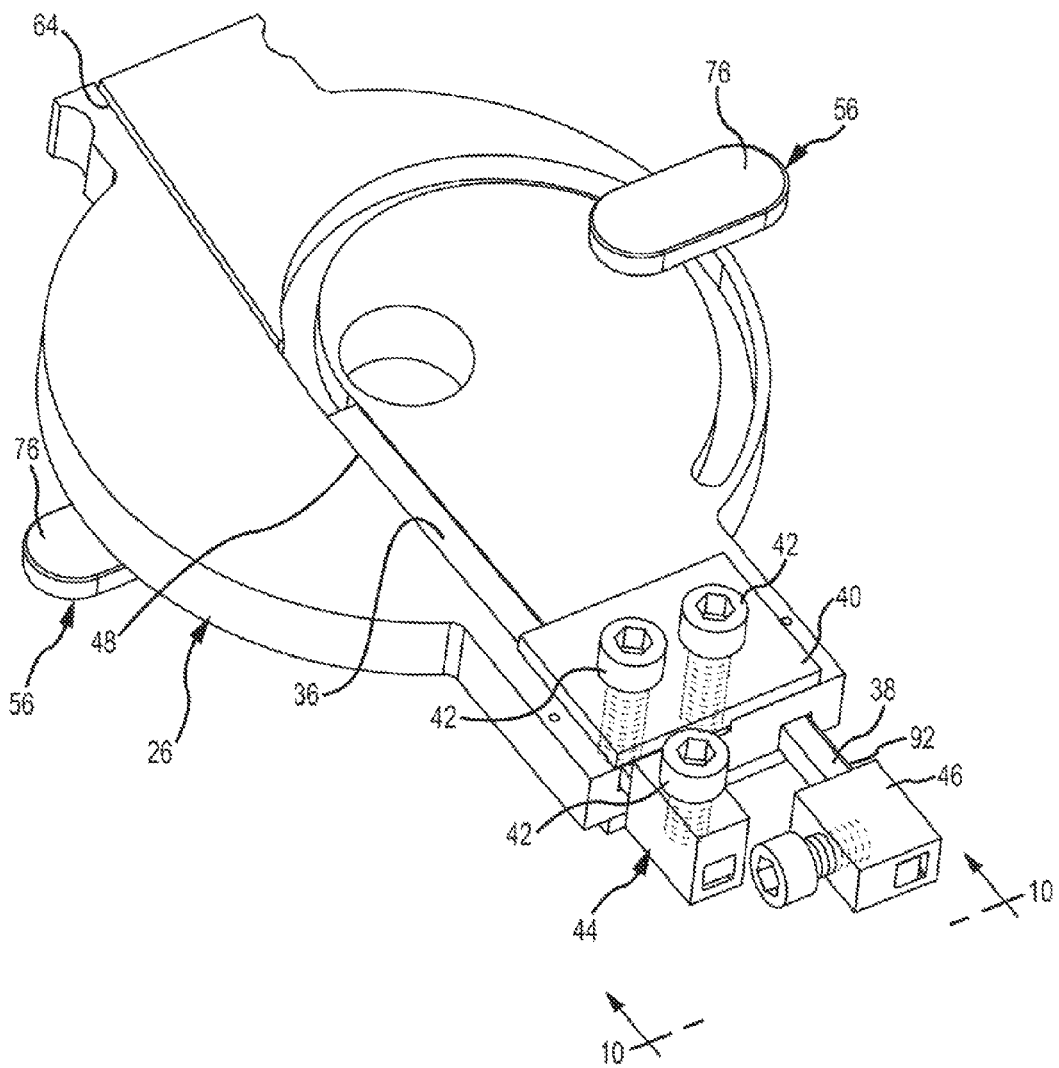
FIG. 9 is an isometric view similar to FIG. 7, but also showing the pull wire arms and their respective retention plates and pull wire clamps.

Referring to FIGS. 8 and 9, a first pull wire (not shown), extending proximally from the deflectable distal end of a medical device, would approach the distal end of pull wire arm guide plate 26 (i.e., the most-upward end of the pull wire guide plate 26 as depicted in FIG. 8), would ride in upper pull wire slot 64, and extend further proximally along slot 64 in arm channel 48, and to the proximal end of the first pull wire arm 36, where the first pull wire would be attached (e.g., clamped) to the proximal end of the first pull wire arm 36 by the first pull wire clamp 44 shown in, for example, FIG. 9). While the thumb boss 28 is being moved from the three o'clock position to the one o'clock position in FIG. 8, the amount of tension in this pull wire is simultaneously increasing as the distal end of the medical device becomes more and more deflected. Thus, by appropriately configuring the shape of the pin groove 52 and the length of the plate channel 78, the mechanical advantage may be increased such that the felt thumb force experienced through application of thumb force 88 is adjusted to physician preference. For example, the pin groove 52 could be configured such that the thumb force 88 remains constant despite the fact that the tension in the pull wire is increasing. Not only is it possible to adjust the pin groove 52 and plate channel 78 configuration in order to maintain relatively constant thumb force 88 throughout use of the medical device, it is also possible to precisely control the amount of felt thumb force. Nevertheless, it may be desirable for the felt thumb force to increase as the deflection of the medical device is increased (e.g., when the clinician pushes the thumb boss 28 from the three o'clock position to the one o'clock position in FIG. 8) to provide meaningful feedback to the clinician that the forces inside of the medical device are increasing as the medical device becomes more and more deflected.

In one embodiment, the drive wheel 24 may be rotated through an angle of 50°. The mechanical advantage in such a system may start at approximately 1.3:1 to 1.6:1 and increase to approximately 1.7:1 to 2.0:1. In addition to controlling the felt thumb force on the thumb bosses 28, 30, it is also possible in this design to control the amount of throw (or longitudinal travel of the pull wire). In one embodiment, for example, a pull wire arm 36 is displaced longitudinally between 0.5 and 0.7 inches.

FIG. 9 is similar to FIG. 7, but depicts both the upper sliding pin carrier 56 and the lower sliding pin carrier 56 in position on the pull wire arm guide plate 26. This figure also shows the first pull wire arm 36 and the second pull wire arm 38 mounted in their respective arm channels 48. The upper pull wire arm retention plate 40 and the lower pull wire arm retention plate 40 are visible. Two cap screws 42 holding the upper pull wire arm retention plate in position on the pull wire arm guide plate 26 are also visible in FIG. 9. A pull wire clamp 44 is shown attached to the proximal end of the first pull wire arm 36 and a second pull wire clamp 46 is depicted attached to the proximal end of the second pull wire arm 38.

Figure 10:
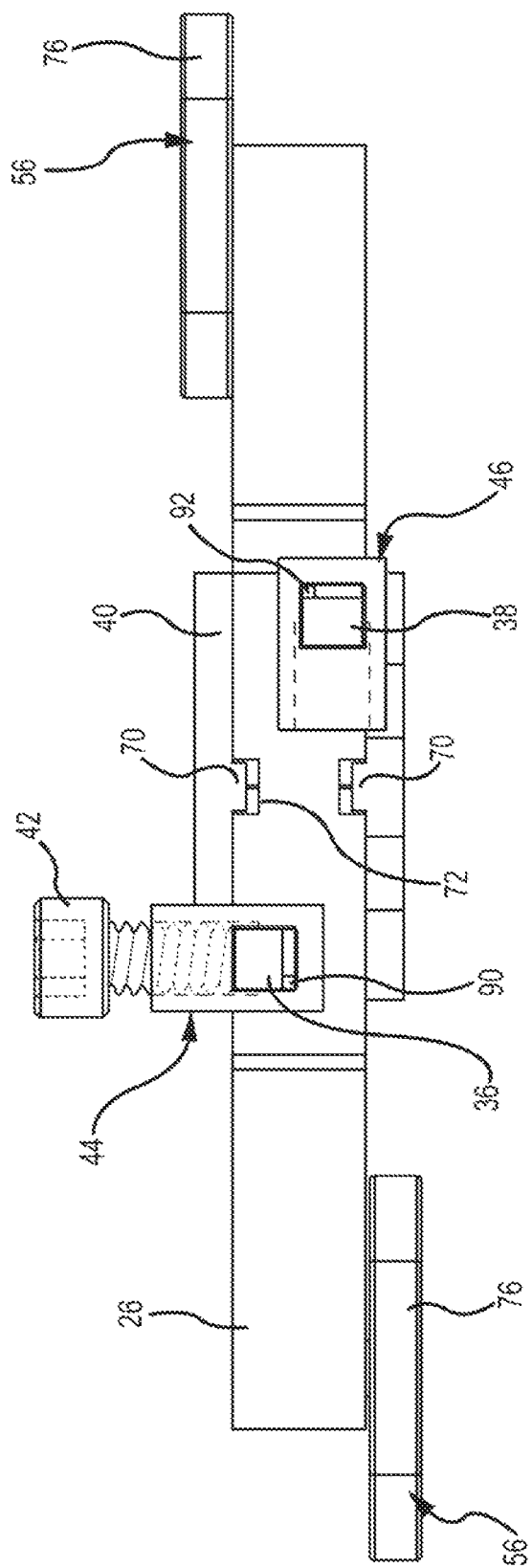
FIG. 10 is an elevation view taken along line 10-10 of FIG. 9

FIG. 10 is an elevation view showing the proximal end of the assembly shown in FIG. 9. In this figure, the rib 70 along the bottom surface of the upper pull wire arm retention plate 40 may be seen. A similar rib 70 is visible extending upwardly from the lower pull wire arm retention plate. As explained above, these ribs can help align and stabilize the retention plates. As may be clearly seen in FIG. 10, each of the pull wire arms 36, 38 includes a longitudinally-extending notch 90, 92, respectively, in which a respective pull wire rides. Once a pull wire is positioned desirably relative to its pull wire arm, the cap screw is tightened to clamp the pull wire so that it moves with the corresponding pull wire arm.

In one embodiment, the pull wire actuator 22 is incorporated into a control handle 10 for a medical device. The control handle 10 incorporating such a pull wire actuator 22 may include a manipulatable actuator, such as drive wheel 24, having an axis of rotation 86. The bendable pushing member 82 is movable with rotation of the drive wheel 24 or other manipulatable actuator. A channel, such as pin groove 52, may be contoured to arcuately advance a back portion (i.e., proximate the elongated plate 76) of the bendable pushing member 82 along a generally decreasing radial path relative to the axis of rotation 86, and further contoured to direct a remaining portion of the bendable pushing member 82 from its generally decreasing radial path to a substantially linear path (i.e., arm channel 48) oriented longitudinally through the control handle 10. A pull wire may be coupled to the remaining portion of the bendable pushing member 82 that is oriented longitudinally through the control handle 10, such as by way of direct coupling to the bendable pushing member 82, or by way of indirect coupling through one or more intermediary components such as first pull wire arm 36. The coupled pull wire can thus be directed substantially longitudinally toward a distal end of the control handle 10. The pull wire may ultimately be provided within a medical device shaft (not shown), whereby rotation of the manipulatable actuator causes tensioning of the pull wire and consequently facilitates deflection of a distal portion of the shaft. As described herein, a mechanical advantage is increasingly provided over at least a portion of the rotation of the manipulatable actuator. The pull wire actuator 22 may include one or more additional replications of such structure to analogously accommodate additional pull wires.

Figure 11:
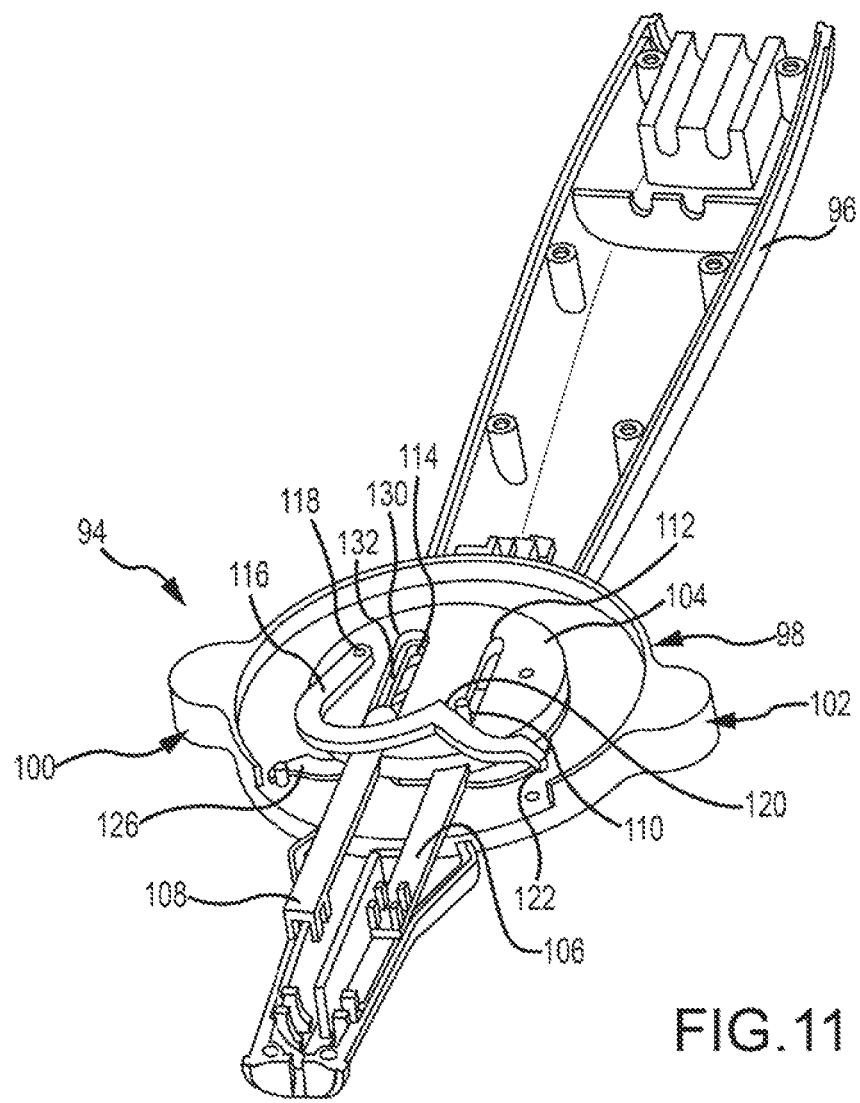
FIG. 11 is an isometric view depicting an alternative pull wire actuator with its top cover removed and mounted in a handle lower housing.

FIGS. 11-17 depict a second pull wire actuator 94 that also provides a mechanical advantage, similar to that provided by the pull wire actuator 22 depicted in FIGS. 1-10. FIG. 11 depicts the second pull wire actuator 94 mounted in a lower handle housing 96. This pull wire actuator 94 also includes a drive wheel 98 having lateral thumb bosses 100, 102 and being pivotable relative to a pull wire arm guide plate 104. This pull wire actuator 94 includes a first pull wire arm 106 and a second pull wire arm 108. These arms are mirror images of each other. As shown in FIG. 11, the first pull wire arm includes a pushed pin 110 that rides in a longitudinally-extending pin channel 112 having a distal end and a proximal end. The second pull wire arm 108 includes a similar pushed pin (not visible in FIG. 11) that rides in a similar longitudinally-extending pin channel 114. This embodiment of the pull wire actuator 94 includes an upper cam arm 116 that is pivotally mounted on the top surface of the pull wire arm guide plate 104. In particular, the upper cam arm 16 is pivotally mounted about a first pivot pin 118 and includes a pushing surface 120 that rides against the pushed pin 110. The upper cam arm also includes a pushed surface 122 against which a pushing pin 124 (not shown in FIG. 11, but is visible in, for example, FIG. 13) pushes. The pushing pin for the upper cam arm is not shown in FIG. 11 because, in this embodiment, the pushing pin extends downwardly from the inside of the drive wheel cover which has been removed in FIG. 11 to reveal the inner workings of the pull arm actuator 94. A lower cam arm 126, which is a mirror image of the upper cam arm 116, is depicted in FIG. 11. It also includes a pushed surface 122' (labeled in FIG. 12) against which a pushing pin 124' pushes. In particular, when the drive wheel 98 is rotated in a first direction 128, a pushing pin 124 pushes on the pushed surface 122 of the upper cam arm 116, whereas when the drive wheel is rotated in the opposite direction, the pushing pin 124' pushes against the pushed surface 122' of the lower cam arm 126.

Figure 12:
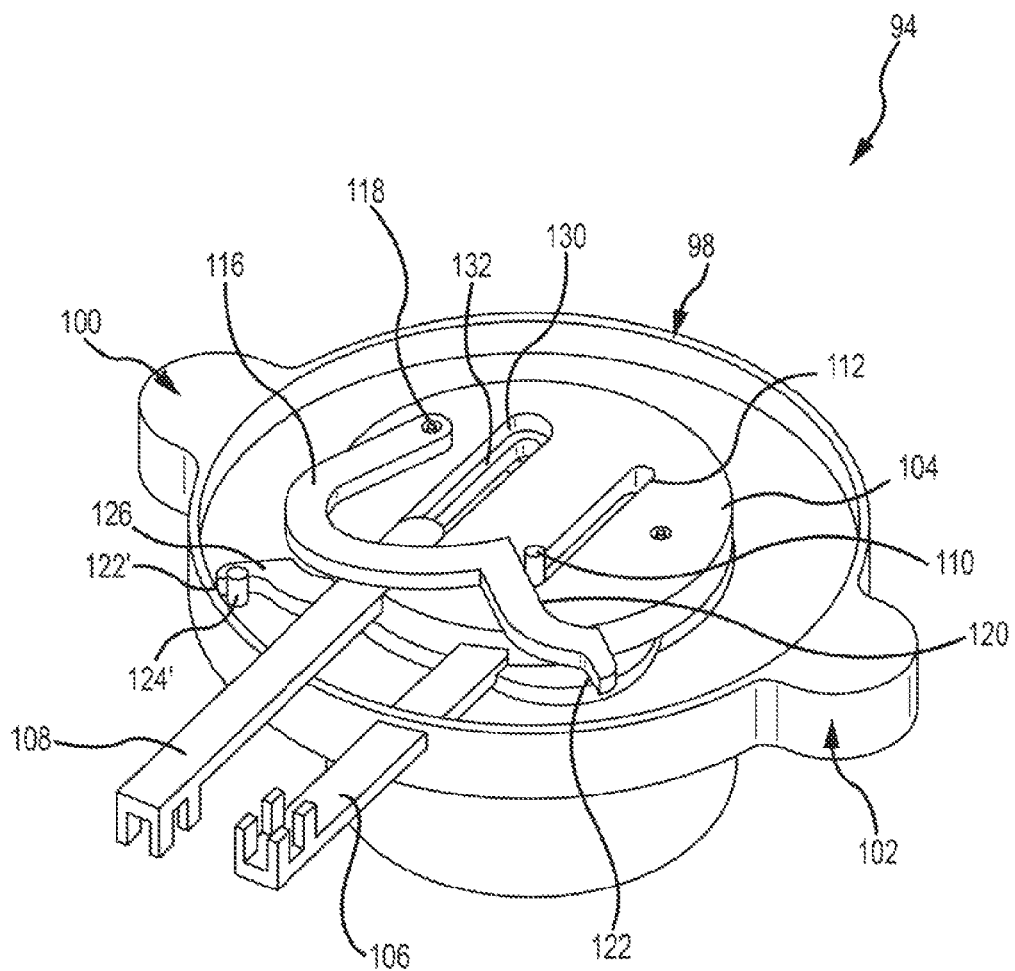
FIG. 12 is an isometric view of the pull wire actuator shown in FIG. 1, but removed from the handle lower housing.

FIG. 12 is a slightly enlarged view of the pull wire actuator 94 shown in FIG. 11. In FIG. 12, however, the pull wire actuator 94 has been removed from the handle lower housing 96. Each of the first and second pull wire arms 106, 108, respectively includes a sliding arm portion slidably engaged in a guide channel 130 on a guiding surface 132 formed in the pull wire arm guide plate 104. The bottom surface of the pull wire arm guide plate 104 is a mirror image of the depicted top surface of the pull wire arm guide plate.

Figure 13:
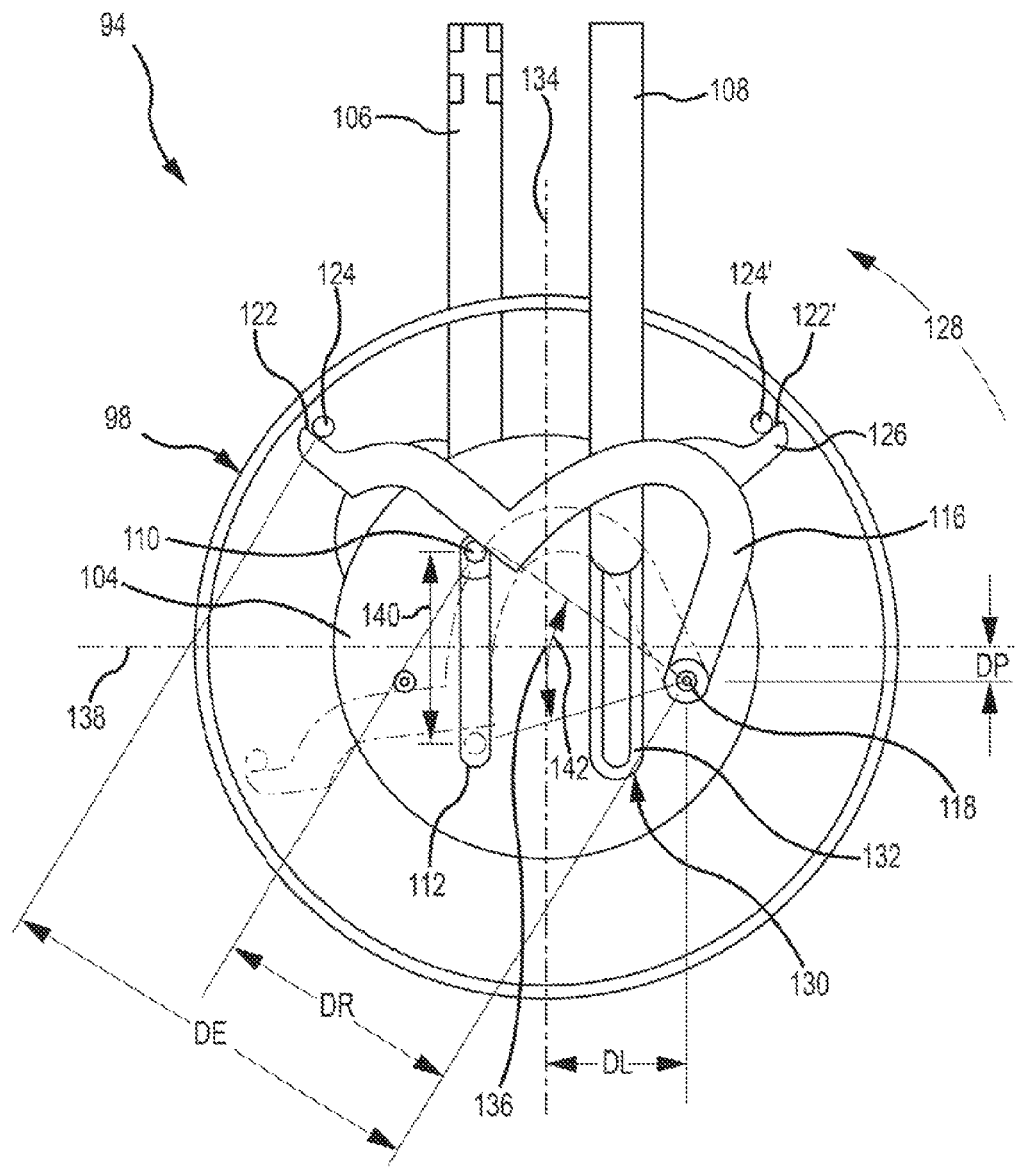
FIG. 13 is a plan view of the pull wire actuator depicted in FIGS. 11 and 12 when the pull wires are in the neutral position (i.e., when the deflectable portion of the catheter (not shown) is in an undeflected configuration).

FIG. 13 is a plan view looking down on the pull wire actuator 94 shown in, for example, FIGS. 11 and 12. This figure clearly shows how the second pull wire arm 108 rides in its guide channel 130 on its guiding surface 132. This figure also shows how the pivot pin 118 for the upper cam arm 116 is displaced laterally a distance DL from longitudinal center line 134 through the axis of rotation 136 of the drive wheel 98 and is displaced proximally a distance DP from the lateral center line 138 through the axis of rotation 136 of the drive wheel. This pivot pin 118 placement relative to the axis of rotation 136 makes it possible to achieve a mechanical advantage, defined as the length of effort arm DE divided by the length of the resistance arm DR. In this design, the mechanical advantage increases as the drive wheel 98 is rotated in the direction of arrow 128 so as to increase the deflection at the distal end of the catheter (not shown). As will be explained further below, this pull wire actuator 94 is also configured such that, the further the actuator is rotated from its neutral position (shown in, for example, FIGS. 13 and 14) to one of its maximum-deflected orientations (see, e.g., FIG. 17), the greater the proportion of the force applied to the cam arm that goes directly toward driving the pushed pin 110 proximally in its pin channel 112. Additionally, the pull wire actuator depicted in FIG. 13 is designed to achieve a pushed pin throw 140 of, preferably, between 0.5 and 0.6 inches while pivoting the pull wire actuator through an angle 142 of approximately 50°.

Figure 14:
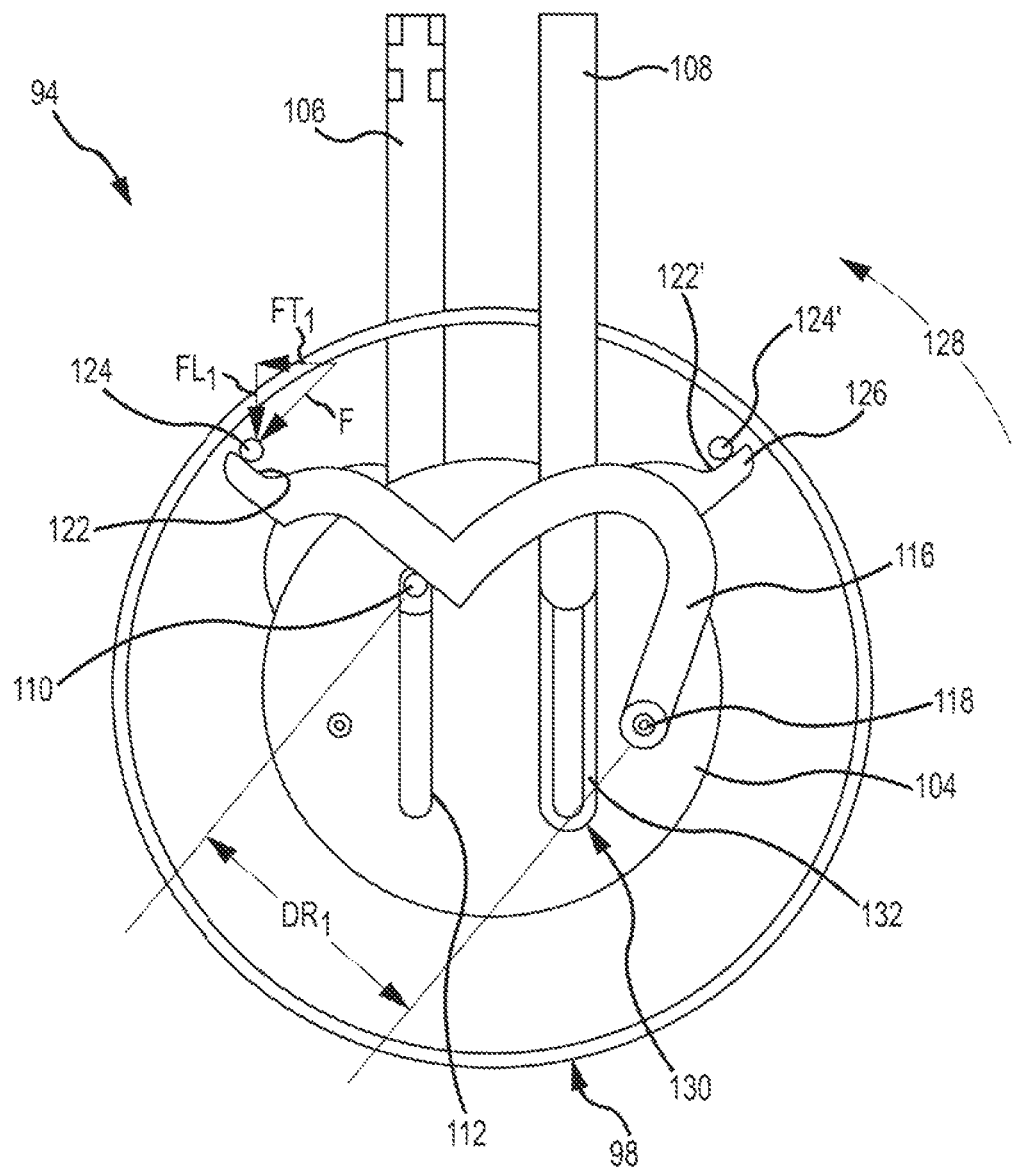
FIGS. 14-17 are similar to FIG. 13 and depict the pull wire actuator of FIGS. 11 and 12 as the first pull wire arm is moved proximally from a neutral position to a fully-retracted position, thereby increasing the deflection of the deflectable catheter shaft (not shown) in a first direction.

Referring now most particularly to FIGS. 14-17, operation of the pull wire actuator 94 according to the embodiment depicted in, for example, FIGS. 11-13, is described next. FIG. 14 is similar to FIG. 13, and shows the pull wire actuator 94 in a catheter-neutral position. In particular, when the first and second pull wire arms 106, 108, respectively, are oriented as shown in FIG. 14 (i.e., with the distal ends of the first and second pull wire arms aligned as also shown in FIG. 13), the distal end of the catheter shaft (not shown) would be in a neutral position (i.e., in a nondeflected position). In this configuration, the distance between the upper cam arm pivot pin 118 and the pushed pin 110 is shown in FIG. 14 as DR, (i.e., length of resistance arm in position 1).

As also shown in FIG. 14, as the pull wire actuator is rotated counterclockwise in the direction of the arrow 128, the pushing pin 124 is forced against the pushed surface 122 of the upper cam arm 116, which starts the upper cam arm to pivot in a counterclockwise direction about its pivot pin 118. The forces being applied by the clinician to the thumb boss 100 (see FIGS. 1L and 12) is represented in FIG. 14 by the force vector F. This force vector F is shown as being resolved into a transverse force component $FT_1$ and a longitudinal force component $FL_1$. As may be understood from this vector diagram, during initiation of counterclockwise rotation of the drive wheel 98 from its neutral position, a relatively high percentage of the total force is being applied in a transverse direction (represented as $FT_1$ in the figure).

Figure 15:
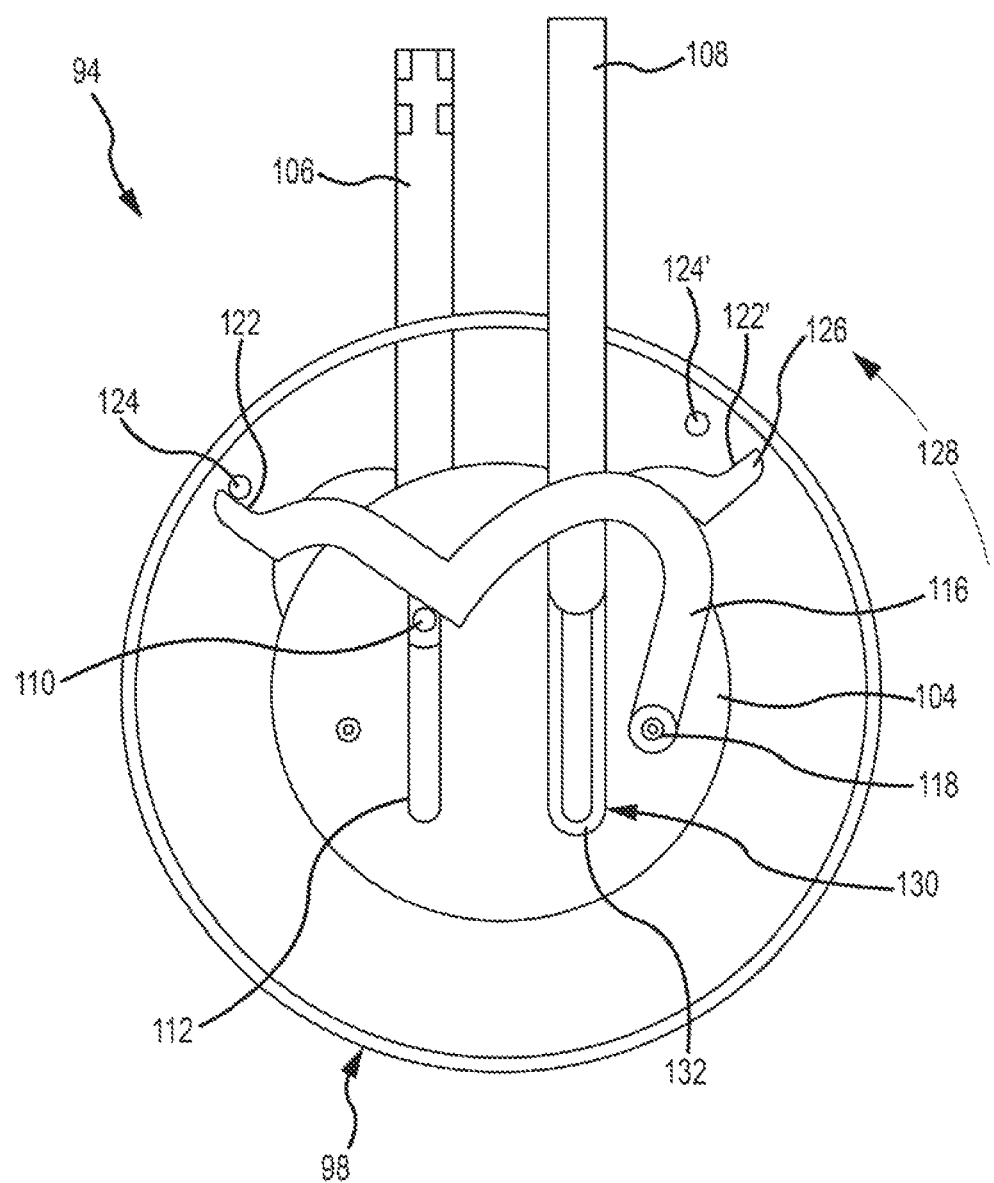

In FIG. 15, the drive wheel 98 has been further rotated in the counterclockwise direction represented by the arrow 128. At this point in the operation of the pull wire actuator 94, the first pull wire arm 106 has been driven proximally (i.e., downwardly in FIG. 15).

Figure 16:
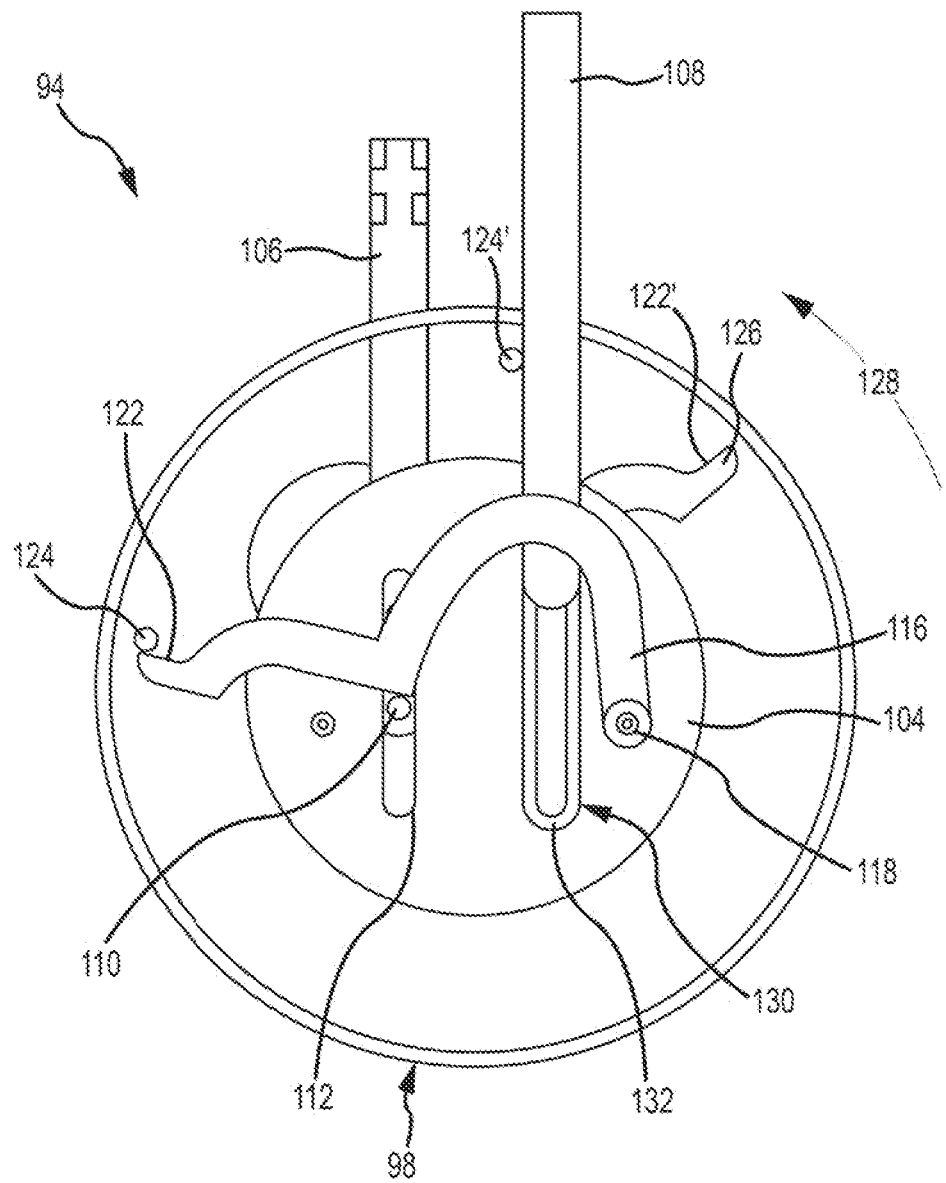

In FIG. 16, the clinician continues to rotate the drive wheel 98 in the counterclockwise direction represented by the arrow 128 in FIG. 16. As may be seen by comparing FIGS. 15 and 16, in this intermediate configuration, the pushed pin 110 on the proximal end of the first pull wire arm 106 has moved further proximally (i.e., downwardly in FIG. 16).

Figure 17:
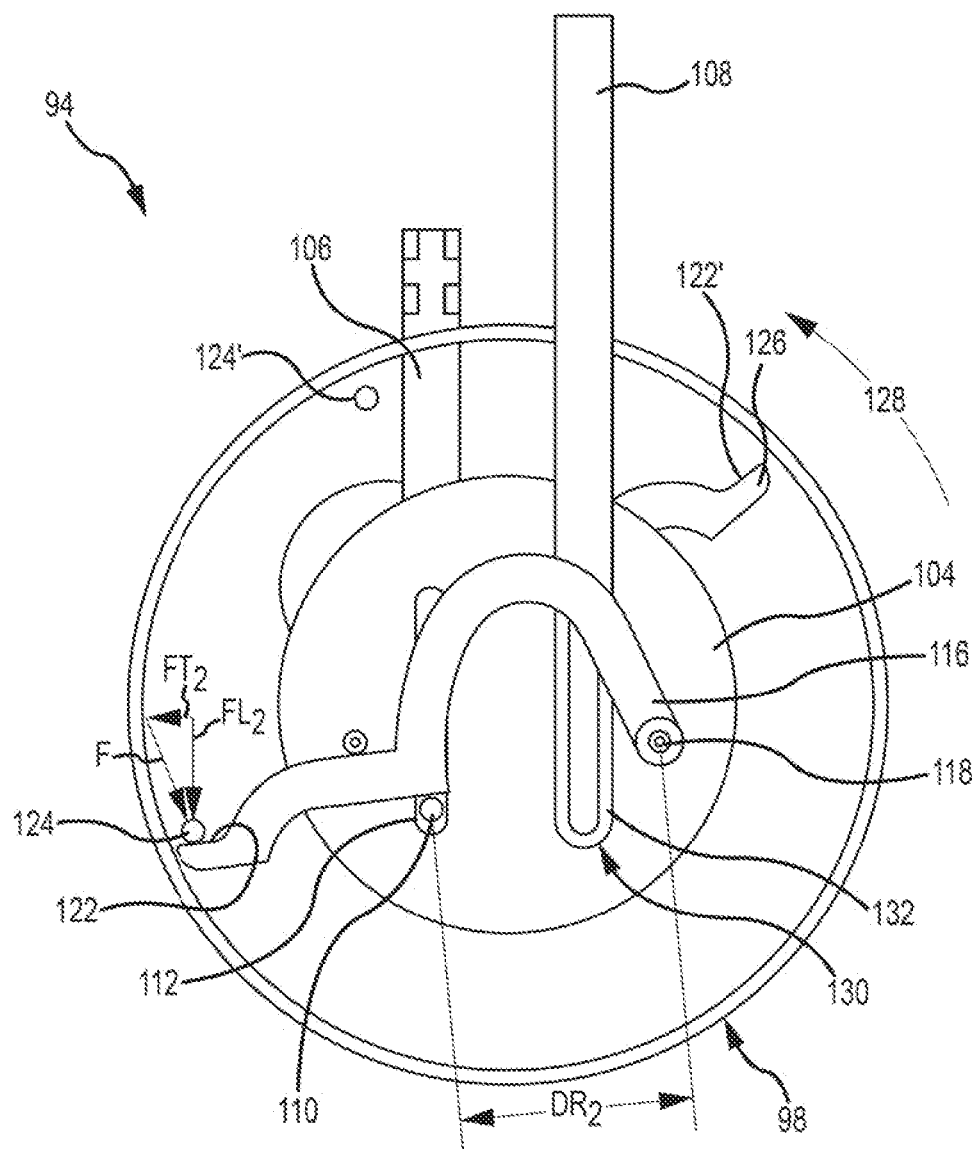

Referring next to FIG. 17, the clinician has continued to rotate the drive wheel 98 counterclockwise in the direction of the arrow 128. At this point, the drive wheel has been rotated approximately 50° from its starting position, the pushed pin 110 has been driven proximally between 0.5 inches and 0.6 inches, and the working end of the catheter shaft (not shown) is in its fully deflected configuration. At this point, the length of the resistance arm has been shortened to the length $DR_2$. Since the distance between the pivot pin 118 and the pushing pin 124 does not change, the mechanical advantage has been increased by shortening the length of the resistance arm to $DR_2$.

As the first pull wire arm 106 has been driven more and more proximally (compare FIGS. 14, 15, 16, and 17), the tension in the pull wire has increased. Simultaneous with that increase in pull wire tension, the mechanical advantage has been increased since the pushed pin 110 has moved closer to the pivot pin 118 of the upper cam arm 116. At the same time, the cam arm is designed such that the vector force F being applied by the pushing pin 124 on the pushed surface 122 of the upper cam arm 116 is contributing more directly to the longitudinal motion of the pushed pin 110 in its guide channel 112. This may be understood by comparing the vector diagram shown in FIG. 17 to the vector diagram shown in FIG. 14. In particular, you will see that even if the vector force F were to remain relatively constant, the longitudinal component $FL_2$ of that vector force in FIG. 17 is greater than the longitudinal component $FL_1$ of the force vector shown in FIG. 14. Thus, a greater portion of the thumb force being applied by the clinician is going directly toward driving the pushed pin 110 on the first pull wire arm 106 proximally in the catheter handle. The longitudinal component of the force F would actually hit its peak when the pushing pin 124 is directly opposite the pivot pin 118 (i.e., somewhere between the position shown in FIG. 16 and the position shown in FIG. 17). The combined effect of capitalizing on applying more of the thumb force in the direction of the desired motion of the pushed pin 110 as well as the increased mechanical advantage, allows this design of a pull wire actuator 94 to maintain, if desired, relatively constant thumb force throughout the full deflection of the deflectable portion of the catheter.

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of all embodiments.

Reference throughout the specification to "various embodiments," "some embodiments," "one embodiment," or "an embodiment," or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial or directional terms such as "vertical," "horizontal," "up," "down," "clockwise," and "counterclockwise" may be used herein with respect to the illustrated embodiments. However, medical instruments may be used in many orientations and positions, and these terms are not intended to be limiting and absolute. Joinder references (e.g., affixed, attached, coupled, connected, and the like) are to be construed broadly and may include intermediate members between a connection of elements and relative movement between elements. As such, joinder references do not necessarily infer that two elements are directly connected and in fixed relation to each other. Changes in detail or structure may be made without departing from the spirit of the invention as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A pull wire actuator comprising the following:
   (a) a pull wire arm guide plate adapted to be mounted in a handle housing, wherein said pull wire arm guide plate comprises the following:
      a top surface and a bottom surface;
      a first arm channel in said top surface, wherein said first arm channel has a distal end and a proximal end; and
      a first arcuate pin groove in said top surface, wherein said first arcuate pin groove extends from a first end to a second end, and wherein said second end of said first arcuate pin groove meets said distal end of said first arm channel;
   (b) a drive wheel attached around said pull wire arm guide plate and pivotable relative to said pull wire arm guide plate, wherein said drive wheel comprises first and second thumb bosses for pivoting said drive wheel about a drive wheel axis of rotation;
   (c) a first pull wire arm slidably mounted in said first arm channel;
   (d) a first sliding pin carrier slidably disposed on said top surface of said pull wire arm guide plate, said first sliding pin carrier comprising a first pushing pin riding in said first arcuate pin groove; and
   (e) a first bendable pushing member slidably positioned in said first arcuate pin groove between said first pushing pin and a distal end of said first pull wire arm;
   wherein said first arcuate pin groove is radially offset from said drive wheel axis of rotation by a first radial distance, and wherein said first radial distance decreases moving from said first end toward said second end of said first arcuate pin groove.

2. The pull wire actuator of claim 1, wherein said first pull wire arm further comprises a first pull wire clamp at a proximal end of said first pull wire arm.

3. The pull wire actuator of claim 1, wherein said pull wire arm guide plate further comprises the following:
- a second arm channel in said bottom surface, wherein said second arm channel has a distal end and a proximal end; and
- a second arcuate pin groove in said bottom surface, wherein said second arcuate pin groove extends from a first end to a second end, and wherein said second end of said second arcuate pin channel meets said distal end of said second arm channel; and said pull wire actuator further comprise the following:
- (f) a second pull wire arm slidably mounted in said second arm channel;
- (g) a second sliding pin carrier slidably disposed on said bottom surface of said pull wire arm guide plate, said second sliding pin carrier comprising a second pushing pin riding in said second arcuate pin groove; and
- (h) a second bendable pushing member slidably positioned in said second arcuate pin groove between said second pushing pin and a distal end of said second pull wire arm.

4. The pull wire actuator of claim 3, wherein said first pull wire arm is movable proximally when said drive wheel is pivoted in a first direction, and wherein said second pull wire arm is movable proximally when said drive wheel is pivoted in a second direction.

5. The pull wire actuator of claim 3, wherein said second arcuate pin groove is radially offset from said drive wheel axis of rotation by a second radial distance, and wherein said second radial distance decreases moving from said first end toward said second end of said second arcuate pin groove.

6. A control handle comprising the following:
- (a) a handle upper housing and a handle lower housing together defining a handle housing;
- (b) a pull wire arm guide plate mounted in said handle housing, wherein said pull wire arm guide plate comprises the following:
  - a top surface and a bottom surface;
  - a first arm channel in said top surface, wherein said first arm channel has a distal end and a proximal end; and
  - a first arcuate pin groove in said top surface, wherein said first arcuate pin groove extends from a first end to a second end, and wherein said second end meets said distal end of said first arm channel;
- (c) a drive wheel attached around said pull wire arm guide plate and pivotable in said handle housing relative to said pull wire arm guide plate, wherein said drive wheel comprises first and second thumb bosses for pivoting said drive wheel about a drive wheel axis of rotation;
- (d) a first pull wire arm slidably mounted in said first arm channel and comprising a proximal end and a distal end;
- (e) a sliding pin carrier slidably disposed on said top surface of said pull wire arm guide plate, said sliding pin carrier comprising a first pushing pin riding in said first arcuate pin groove; and
- (f) a first bendable pushing member slidably positioned in said first arcuate pin groove between said first pushing pin and said distal end of said first pull wire arm;
wherein said first arcuate pin groove is radially offset from said drive wheel axis of rotation by a first radial distance, and wherein said first radial distance decreases moving from said first end toward said second end of said first arcuate pin groove.

7. The control handle of claim 6, wherein said pull wire arm guide plate has a distal end and a proximal end, and wherein said pull wire arm guide plate further comprises a first pull wire slot in said top surface and extending from said pull wire arm guide plate distal end to said distal end of said first arm channel; and
wherein said control handle further comprises a pull wire extending proximally from a proximal end of said pull wire slot, through said first arm channel to a proximal end of said first pull wire arm where said pull wire is affixed to said first pull wire arm for movement therewith.

8. The control handle of claim 6 further comprising an upper pull wire arm retention plate to slidably retain said first pull wire arm in said first arm channel.

9. The control handle of claim 6, wherein said drive wheel further comprise a top half and a bottom half, wherein said top half and said bottom half are attached around said pull wire arm guide plate, and wherein said top half of said drive wheel defines a plate channel, and wherein said sliding pin carrier further comprises an elongated plate adapted to slide in said plate channel.

10. The control handle of claim 9, wherein said plate channel is radially oriented relative to said drive wheel axis of rotation, whereby said sliding pin carrier can slide radially inwardly and outwardly toward and away from, respectively, said drive wheel axis of rotation as said drive wheel is pivoted in first and second directions, respectively.

11. The control handle of claim 9, wherein said bottom half of said drive wheel further comprise a plate positioner adapted to retain said elongated plate of said sliding pin carrier in said plate channel in said top half of said drive wheel.

12. A pull wire actuator comprising the following:
- (a) a pull wire arm guide plate adapted to be mounted in a handle housing, wherein said pull wire arm guide plate comprises the following:
  - a top surface and a bottom surface;
  - a first arm channel in said top surface, wherein said first arm channel has a distal end and a proximal end; and
  - a first longitudinally-extending pin channel through said top surface, wherein said first longitudinally-extending pin channel extends from a distal end to a proximal end;
- (b) a drive wheel attached around said pull wire arm guide plate and pivotable relative to said pull wire arm guide plate, wherein said drive wheel comprises (i) first and second thumb bosses for pivoting said drive wheel about a drive wheel axis of rotation, and (ii) a first pushing pin;
- (c) a first pull wire arm slidably mounted in said first arm channel, wherein said first pull wire arm comprises a proximal end, a distal end, and a first pushed pin riding in said first longitudinally-extending pin channel; and
- (d) a first cam arm pivotally mounted on said top surface of said pull wire arm guide plate at a first pivot pin, wherein said first pivot pin is both laterally and longitudinally offset from said drive wheel axis of rotation, and wherein said first cam arm comprises (i) a first pushing surface adapted to push against said first pushed pin, and (ii) a first pushed surface against which said first pushing pin is adapted to push;
wherein a separation distance between said first pushed pin and said first pivot pin decreases as said drive wheel is rotated from a catheter-neutral orientation to a first catheter-deflected orientation.

13. The pull wire actuator of claim 12, wherein said pull wire arm guide plate further comprises the following:
- a second arm channel in said bottom surface, wherein said second arm channel has a distal end and a proximal end; and a second longitudinally-extending pin channel through said bottom surface, wherein said second longitudinally-extending pin channel extends from a distal end to a proximal end; and said pull wire actuator further comprise the following:

(e) a second pull wire arm slidably mounted in said second arm channel, wherein said second pull wire arm comprises a proximal end, a distal end, and a second pushed pin riding in said second longitudinally-extending pin channel; and (f) a second cam arm pivotally mounted on said bottom surface of said pull wire arm guide plate at a second pivot pin, wherein said second pivot pin is both laterally and longitudinally offset from said drive wheel axis of rotation, and wherein said second cam arm comprises (i) a second pushing surface adapted to push against said second pushed pin, and (ii) a second pushed surface against which said second pushing pin is adapted to push;

wherein a separation distance between said second pushed pin and said second pivot pin decreases as said drive wheel is rotated from said catheter-neutral orientation to a second catheter-deflected orientation.

14. A control handle comprising the following:
(a) a handle upper housing and a handle lower housing together defining a handle housing;
(b) a pull wire arm guide plate mounted in said handle housing, wherein said pull wire arm guide plate comprises the following:
   a top surface and a bottom surface;
   a first arm channel in said top surface, wherein said first arm channel has a distal end and a proximal end; and
   a first longitudinally-extending pin channel through said top surface, wherein said pin channel extends from a distal end to a proximal end;
(c) a drive wheel attached around said pull wire arm guide plate and pivotable relative to said pull wire arm guide plate, wherein said drive wheel comprises (i) first and second thumb bosses for pivoting said drive wheel about a drive wheel axis of rotation, and (ii) a first pushing pin;
(d) a first pull wire arm slidably mounted in said first arm channel, wherein said first pull wire arm comprises a proximal end, a distal end, and a first pushed pin riding in said first longitudinally-extending pin channel; and
(e) a first cam arm pivotally mounted on said top surface of said pull wire arm guide plate at a first pivot pin, wherein said first pivot pin is both laterally and longitudinally offset from said drive wheel axis of rotation, and wherein said first cam arm comprises (i) a first pushing surface adapted to push against said first pushed pin, and (ii) a first pushed surface against which said first pushing pin is adapted to push;
wherein a separation distance between said first pushed pin and said first pivot pin decreases as said drive wheel is rotated from a catheter-neutral orientation to a first catheter-deflected orientation.

15. The control handle of claim 14, wherein a first pull wire is attached to said distal end of said first pull wire arm for movement therewith, and wherein said first pull wire extends distally from said control handle.

16. The control handle of claim 14, wherein said drive wheel further comprise a top half and a bottom half, wherein said top half and said bottom half are attached around said pull wire arm guide plate.

17. A pull wire actuator comprising the following:
(a) a pull wire arm guide plate adapted to be mounted in a handle housing, wherein said pull wire arm guide plate comprises the following:
   a top surface and a bottom surface;
   a first arm channel in said top surface, wherein said first arm channel has a distal end and a proximal end;
   a first longitudinally-extending pin channel through said top surface, wherein said first longitudinally-extending pin channel extends from a distal end to a proximal end;
   a second arm channel in said bottom surface, wherein said second arm channel has a distal end and a proximal end; and
   a second longitudinally-extending pin channel through said bottom surface, wherein said second longitudinally-extending pin channel extends from a distal end to a proximal end;
(b) a drive wheel attached around said pull wire arm guide plate and pivotable relative to said pull wire arm guide plate, wherein said drive wheel comprises (i) first and second thumb bosses for pivoting said drive wheel about a drive wheel axis of rotation, and (ii) a first pushing pin;
(c) a first pull wire arm slidably mounted in said first arm channel, wherein said first pull wire arm comprises a proximal end, a distal end, and a first pushed pin riding in said first longitudinally-extending pin channel;
(d) a first cam arm pivotally mounted on said top surface of said pull wire arm guide plate at a first pivot pin, wherein said first pivot pin is both laterally and longitudinally offset from said drive wheel axis of rotation, and wherein said first cam arm comprises (i) a first pushing surface adapted to push against said first pushed pin, and (ii) a first pushed surface against which said first pushing pin is adapted to push;
(e) a second pull wire arm slidably mounted in said second arm channel, wherein said second pull wire arm comprises a proximal end, a distal end, and a second pushed pin riding in said second longitudinally-extending pin channel; and
(f) a second cam arm pivotally mounted on said bottom surface of said pull wire arm guide plate at a second pivot pin, wherein said second pivot pin is both laterally and longitudinally offset from said drive wheel axis of rotation, and wherein said second cam arm comprises (i) a second pushing surface adapted to push against said second pushed pin, and (ii) a second pushed surface against which said second pushing pin is adapted to push.

18. The pull wire actuator of claim 17, wherein said first pivot pin is positioned so that a mechanical advantage of said first cam arm increases as said drive wheel is rotated from a catheter-neutral orientation to a first catheter-deflected orientation.

19. The pull wire actuator of claim 17, wherein said second pivot pin is positioned so that a mechanical advantage of said second cam arm increases as said drive wheel is rotated from a catheter-neutral orientation to a second catheter-deflected orientation.

20. The pull wire actuator of claim 17, wherein said first and second pivot pins are positioned laterally from said drive wheel axis of rotation on opposite sides of an actuator longitudinal axis, and wherein said first and second pivot pins are positioned proximally of said drive wheel axis of rotation.

21. The pull wire actuator of claim 17, wherein said first pull wire arm is movable proximally when said drive wheel is pivoted in a first direction, and wherein said second pull wire arm is movable proximally when said drive wheel is pivoted in a second direction.

22. A control handle comprising the following:
(a) a handle upper housing and a handle lower housing together defining a handle housing;
(b) a pull wire arm guide plate mounted in said handle housing, wherein said pull wire arm guide plate comprises the following:
a top surface and a bottom surface;
a first arm channel in said top surface, wherein said first arm channel has a distal end and a proximal end; and
a first arcuate pin groove in said top surface, wherein said first arcuate pin groove extends from a first end to a second end, and wherein said second end meets said distal end of said first arm channel;
(c) a drive wheel attached around said pull wire arm guide plate and pivotable in said handle housing relative to said pull wire arm guide plate, wherein said drive wheel comprises first and second thumb bosses for pivoting said drive wheel about a drive wheel axis of rotation;
(d) a first pull wire arm slidably mounted in said first arm channel and comprising a proximal end and a distal end;
(e) a sliding pin carrier slidably disposed on said top surface of said pull wire arm guide plate, said sliding pin carrier comprising a first pushing pin riding in said first arcuate pin groove; and
(f) a first bendable pushing member slidably positioned in said first arcuate pin groove between said first pushing pin and said distal end of said first pull wire arm;
wherein said drive wheel further comprise a top half and a bottom half; wherein said top half of said drive wheel defines a plate channel; wherein said sliding pin carrier further comprises an elongated plate adapted to slide in said plate channel; and wherein said plate channel is radially oriented relative to said drive wheel axis of rotation, whereby said sliding pin carrier can slide radially inwardly and outwardly toward and away from, respectively, said drive wheel axis of rotation as said drive wheel is pivoted in first and second directions, respectively.

23. The control handle of claim 22, wherein said pull wire arm guide plate has a distal end and a proximal end; wherein said pull wire arm guide plate further comprises a first pull wire slot in said top surface and extending from said pull wire arm guide plate distal end to said distal end of said first arm channel; and wherein said control handle further comprises a pull wire extending proximally from a proximal end of said pull wire slot, through said first arm channel to a proximal end of said first pull wire arm where said pull wire is affixed to said first pull wire arm for movement therewith.

24. A pull wire actuator comprising the following:
(a) a pull wire arm guide plate adapted to be mounted in a handle housing, wherein said pull wire arm guide plate comprises the following:
a top surface and a bottom surface;
a first arm channel in said top surface, wherein said first arm channel has a distal end and a proximal end;
a first arcuate pin groove in said top surface, wherein said first arcuate pin groove extends from a first end to a second end, and wherein said second end of said first arcuate pin groove meets said distal end of said first arm channel;
a second arm channel in said bottom surface, wherein said second arm channel has a distal end and a proximal end; and
a second arcuate pin groove in said bottom surface, wherein said second arcuate pin groove extends from a first end to a second end, and wherein said second end of said second arcuate pin channel meets said distal end of said second arm channel;
(b) a drive wheel attached around said pull wire arm guide plate and pivotable relative to said pull wire arm guide plate, wherein said drive wheel comprises first and second thumb bosses for pivoting said drive wheel about a drive wheel axis of rotation;
(c) a first pull wire arm slidably mounted in said first arm channel;
(d) a first sliding pin carrier slidably disposed on said top surface of said pull wire arm guide plate, said first sliding pin carrier comprising a first pushing pin riding in said first arcuate pin groove;
(e) a first bendable pushing member slidably positioned in said first arcuate pin groove between said first pushing pin and a distal end of said first pull wire arm.
(f) a second pull wire arm slidably mounted in said second arm channel;
(g) a second sliding pin carrier slidably disposed on said bottom surface of said pull wire arm guide plate, said second sliding pin carrier comprising a second pushing pin riding in said second arcuate pin groove; and
(h) a second bendable pushing member slidably positioned in said second arcuate pin groove between said second pushing pin and a distal end of said second pull wire arm.

25. The pull wire actuator of claim 24, wherein said first pull wire arm is movable proximally when said drive wheel is pivoted in a first direction, and wherein said second pull wire arm is movable proximally when said drive wheel is pivoted in a second direction.

* * * * *